United States Patent [19]

Cox et al.

[11] Patent Number: 5,165,101

[45] Date of Patent: Nov. 17, 1992

[54] METHODS AND APPARATUS FOR OPTICALLY DETERMINING THE ACCEPTABILITY OF PRODUCTS

[75] Inventors: Kenneth A. Cox; Henry M. Dante; Charles N. Harward; Robert J. Maher, all of Midlothian, Va.

[73] Assignee: Philip Morris Incoporated, New York, N.Y.

[21] Appl. No.: 696,004

[22] Filed: May 6, 1991

Related U.S. Application Data

[63] Continuation-in-part of Ser. No. 634,110, Dec. 17, 1990, abandoned, which is a continuation of Ser. No. 308,739, Feb. 9, 1989, Pat. No. 5,046,111.

[51] Int. Cl.⁵ .............................................. G06K 9/00
[52] U.S. Cl. ...................................... 382/8; 358/101; 358/106; 358/107
[58] Field of Search ................ 382/8, 14, 15, 39; 364/552; 358/101, 106, 107

[56] References Cited

U.S. PATENT DOCUMENTS

| | | | |
|---|---|---|---|
| 3,835,332 | 9/1974 | Bridges | 250/563 |
| 4,053,056 | 10/1977 | Day | 209/73 |
| 4,097,845 | 6/1978 | Bacus | 340/146.3 |
| 4,481,664 | 11/1984 | Linger et al. | 382/8 |
| 4,482,971 | 11/1984 | Blazek | 364/552 |
| 4,637,054 | 1/1987 | Hashim | 382/8 |
| 4,759,074 | 7/1988 | Iadipaola et al. | 382/23 |
| 4,859,863 | 8/1989 | Schrader et al. | 382/8 |
| 4,872,024 | 10/1989 | Nagai et al. | 346/1.1 |
| 4,912,554 | 3/1990 | Neri | 358/106 |
| 4,926,491 | 5/1990 | Maeda et al. | 382/14 |
| 4,952,062 | 8/1990 | Bean, III et al. | 356/430 |
| 4,972,262 | 11/1990 | Nichols | 358/160 |
| 4,972,494 | 11/1990 | White et al. | 382/8 |
| 4,974,261 | 11/1990 | Nakahara et al. | 382/22 |
| 4,975,971 | 12/1990 | Ohnishi | 382/8 |
| 4,975,972 | 12/1990 | Bose et al. | 382/8 |
| 5,007,096 | 4/1991 | Yoshida | 382/8 |
| 5,046,111 | 9/1991 | Cox et al. | 382/8 |

FOREIGN PATENT DOCUMENTS 0155789 1/1985 European Pat. Off. .
0330495 2/1989 European Pat. Off. .
63-257083 10/1988 Japan .
WO89/10596 5/1989 World Int. Prop. O. .

OTHER PUBLICATIONS

J. Schurmann et al., "Erkennungssysteme furdie Zellbild-Analyse zur Krebsfruherkennung," *Wissenschaftliche Berichte AEG.*

R. C. Gonzalez, *Digital Image Processing*, Addison-Wesley Publishing Company, 1987, pp. 331–341.

W. K. Pratt, *Digital Image Processing*, John Wiley & Sons, Inc., 1978, pp. 478–492.

G. H. Golub et al., "Generalized Cross-Validation as a Method for Choosing a Good Ridge Parameter," *Technometrics*, vol. 21, No. May 2, 1979.

*Primary Examiner*—Jose Couso
*Attorney, Agent, or Firm*—Robert R. Jackson

[57] ABSTRACT

The appearance of a product is determined to be acceptable or unacceptable by computing a discriminant function or image from a plurality of two-dimensional images of products of the kind to be inspected. A two-dimensional image of the product is then formed and processed using the discriminant image to produce an output value which can be compared to a predetermined value used in computing the discriminant image. If the output value deviates from the predetermined value by more than a predetermined amount, the product has been found to have an unacceptable appearance.

47 Claims, 19 Drawing Sheets

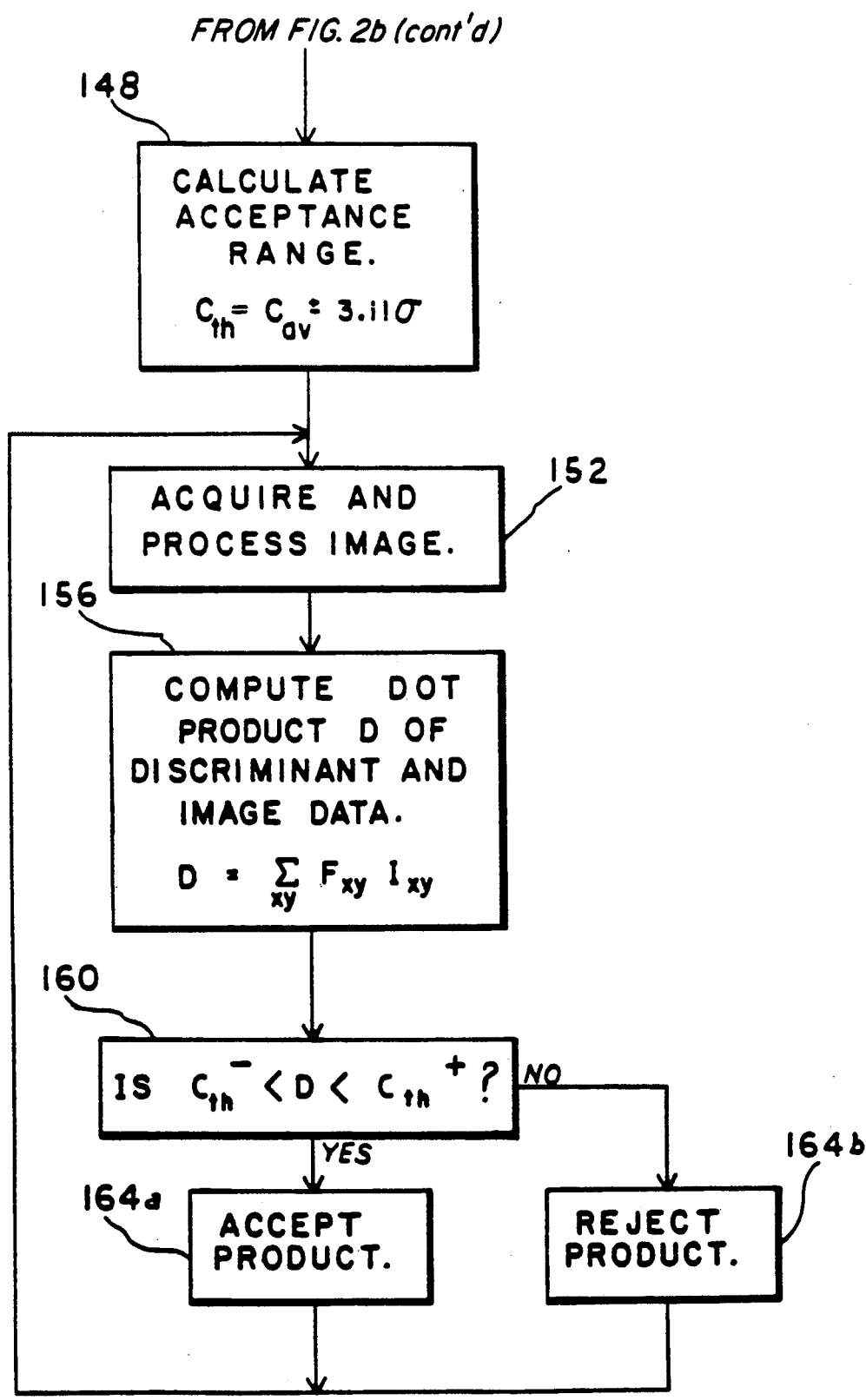

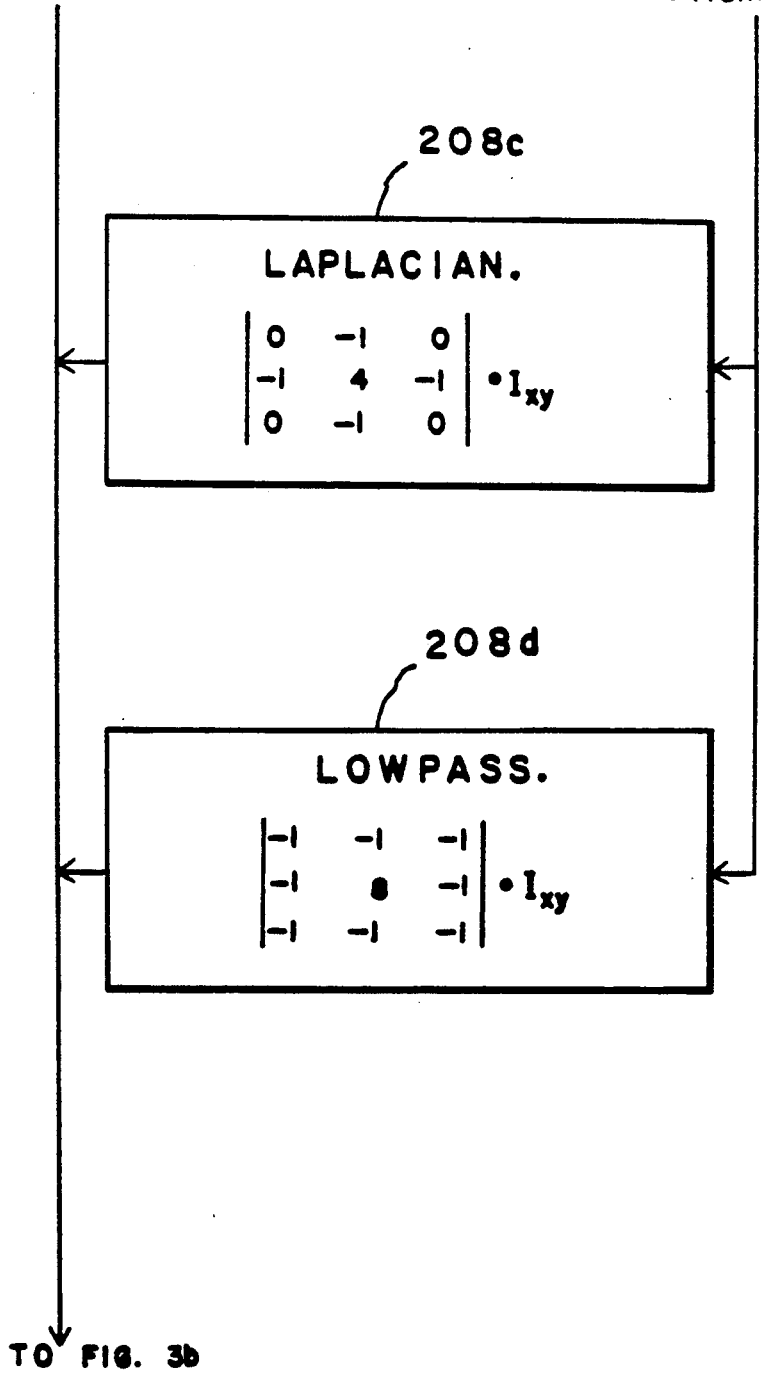

|||||
|||||
01234----
01234----
01234----
01234----
```

$$\begin{pmatrix} 1 & 0 & 0 & 0 & --- \\ 0 & 1 & 0 & 0 & --- \\ 0 & 0 & 1 & 0 & --- \\ & | & | & | & | \\ & | & | & | & | \end{pmatrix}$$

FIG. 12

$$\begin{pmatrix} \gamma_1 & 0 & 0 & 0 & --- \\ 0 & \gamma_2 & 0 & 0 & --- \\ 0 & 0 & \gamma_3 & 0 & --- \\ & | & | & | & | \\ & | & | & | & | \end{pmatrix}$$

METHODS AND APPARATUS FOR OPTICALLY DETERMINING THE ACCEPTABILITY OF PRODUCTS

BACKGROUND OF THE INVENTION

This application is a continuation-in-part of application Ser. No. 634,110, filed Dec. 17, 1990, now abandoned, which is a continuation of application Ser. No. 307,739, filed Feb. 9, 1989, now U.S. Pat. No. 5,046,111.

This invention relates to product inspection methods and apparatus, and more particularly to methods and apparatus for optically determining whether or not a product has an acceptable appearance.

For many products such as consumer goods like packaged foods, beverages, cleaning products, health and beauty aids, cigarettes, cigars, etc., it is very important that the external appearance of the product or its packaging be uniform and defect-free. Yet these products are typically produced in such large quantities and at such high speeds that some form of automated optical inspection is practically essential. Many prior art optical inspection techniques rely on examining only preselected parts of the object being inspected. It is therefore possible for such prior art systems to miss defects occurring in regions other than those preselected for examination, and/or to miss defects of a kind that were not anticipated when the system was set up. Such prior art systems must also be customized for each product inspection task. This requires a high level of skill and is very time-consuming.

In view of the foregoing, it is an object of this invention to provide optical product inspection methods and apparatus which process an overall image of the product being inspected so that a significant defect or deviation from the norm occurring anywhere in the image will cause the associated product to be identified as deviant or defective.

It is another object of this invention to provide optical product inspection methods and apparatus which are of universal application and which can automatically adapt to each new inspection task without requiring elaborate set-up by a highly skilled operator.

It is still another object of this invention to provide optical product inspection methods and apparatus which can automatically acquire the information required to perform each new inspection task without the intervention of a highly skilled operator.

SUMMARY OF THE INVENTION

These and other objects of the invention are accomplished in accordance with the principles of the invention by providing methods and apparatus which compute a filter function or discriminant image from two-dimensional images of a plurality of objects of the kind to be inspected. The discriminant image computation preferably includes a procedure for automatically determining the optimum amount of information from the two-dimensional images to be employed in computing the discriminant image to avoid the introduction of "noise" into the discriminant image which would diminish its effectiveness. After the discriminant image has been computed, a two-dimensional image of each product is formed and processed using the discriminant image to produce an output value which can be compared to a predetermined value used in computing the discriminant image. The appearance of the product is determined to be normal or acceptable if the output value does not deviate from the predetermined value by more than a predetermined amount. Otherwise, the appearance of the product is determined to be non-normal or unacceptable.

Further features of the invention, its nature and various advantages will be more apparent from the accompanying drawings and the following detailed description of the preferred embodiments.

BRIEF DESCRIPTION OF THE DRAWINGS

FIGS. 2a, 2b, and 2c (referred to collectively as FIG. 2) are a flow chart of the optical product inspection method of this invention.

FIGS. 7, 8, 9, and 10 are simplified representations of frame data useful in explaining further image processing steps in accordance with this invention.

FIGS. 11 and 12 show matrices useful in explaining computations performed in accordance with this invention.

DETAILED DESCRIPTION OF THE PREFERRED EMBODIMENTS

In the following Section A of the detailed description, the "basic system" of this invention will be described. Thereafter, in Sections B-E, various optional alternatives or enhancements to the basic system are described. Finally, Section F describes illustrative systems employing certain features of the basic system with various combinations of the alternatives or enhancements described in Sections B-E.

A. The Basic System

Figure 1:
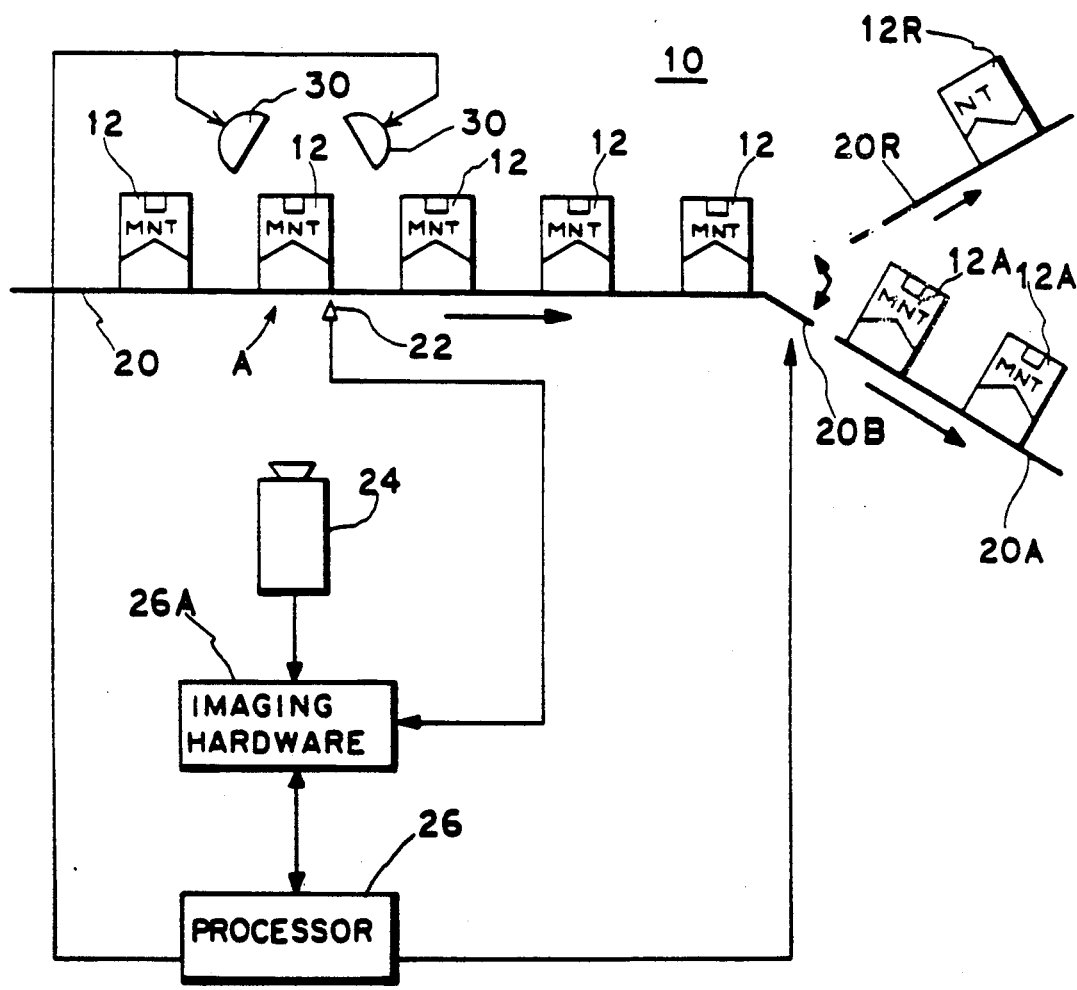
FIG. 1 is a simplified schematic block diagram of an optical product inspection apparatus constructed in accordance with the principles of this invention.

As shown in FIG. 1, typical product inspection apparatus 10 constructed in accordance with this invention includes conveyor apparatus 20 for conveying the objects or products 12 to be inspected, one after another, from left to right as viewed in the FIG. At location A (which is in the field of view of conventional video camera 24) a product 12 is illuminated by light from conventional light sources 30. Each time conventional product sensor 22 detects a product 12 opposite camera 24, imaging hardware 26A (which may be part of processor 26) "grabs" or acquires a two-dimensional image of the product from camera 24. Camera 24 may be a conventional monochrome (e.g., black and white) or polychrome (i.e., color) video camera such as any NTSC or RGB compatible camera. Although it will be apparent to those skilled in the art how the invention can be extended to full color product inspection, for simplicity and clarity only monochrome (e.g., black and white) inspection will be described in detail herein.

Each two-dimensional image acquired by imaging hardware 26A is processed by elements 26 and 26A as described in detail below so that by the time the associated product 12 reaches the controllable branch 20B in conveyor 20, processor 26 has determined whether or not that product has an acceptable image. If the product has an acceptable image, processor 26 controls branch 20B so that the product is directed to conveyor segment 20A which conveys accepted products 12A away for further normal processing. On the other hand, if the product's image is not acceptable, processor 26 controls branch 20B so that the product is directed to conveyor segment 20R which conveys defective and therefore rejected products 12R away for further special handling. Processor 26 is typically a suitably programmed conventional micro- or minicomputer such as a Sun 3/160 workstation available from Sun Microsystems, Inc. of Mountain View, Calif. with a conventional ICS-400 imaging hardware system 26A available from Androx Corporation of Canton, Massachusetts.

Figure 2A:
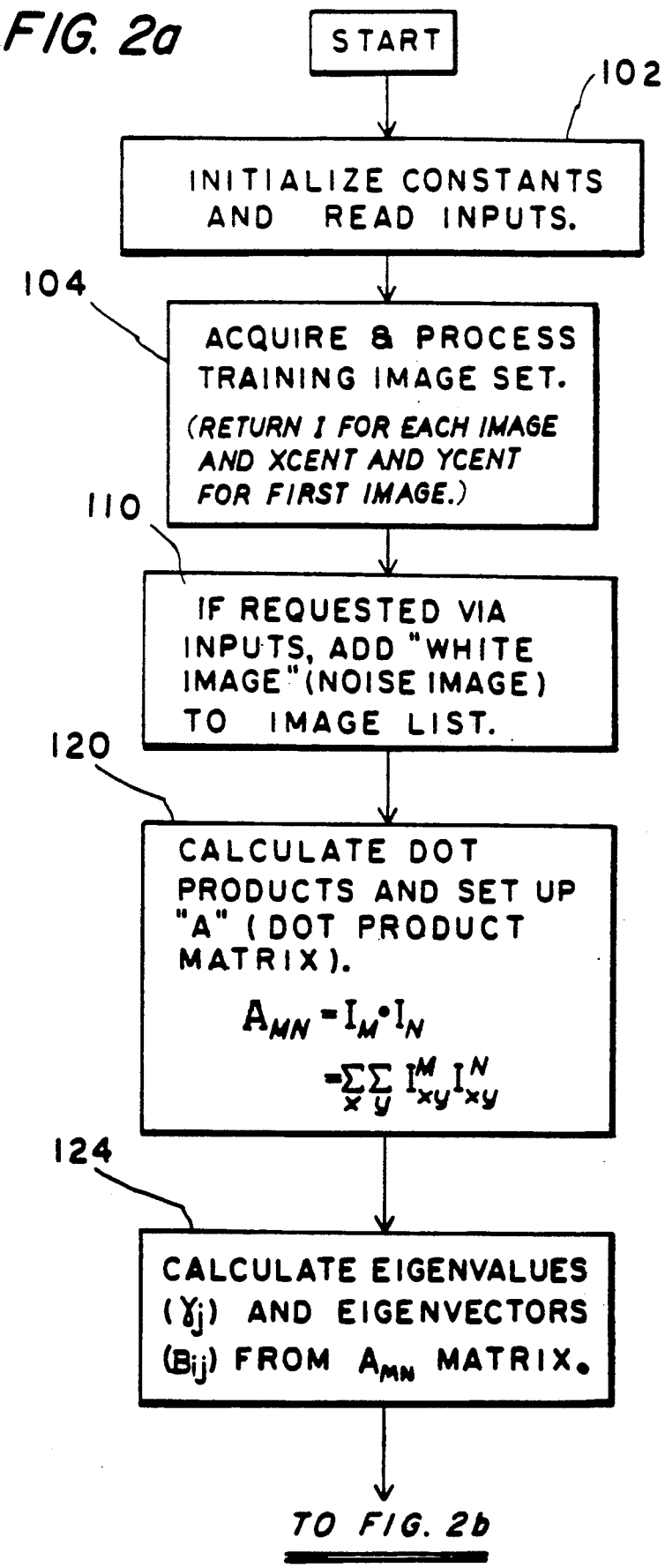
Figure 2B:
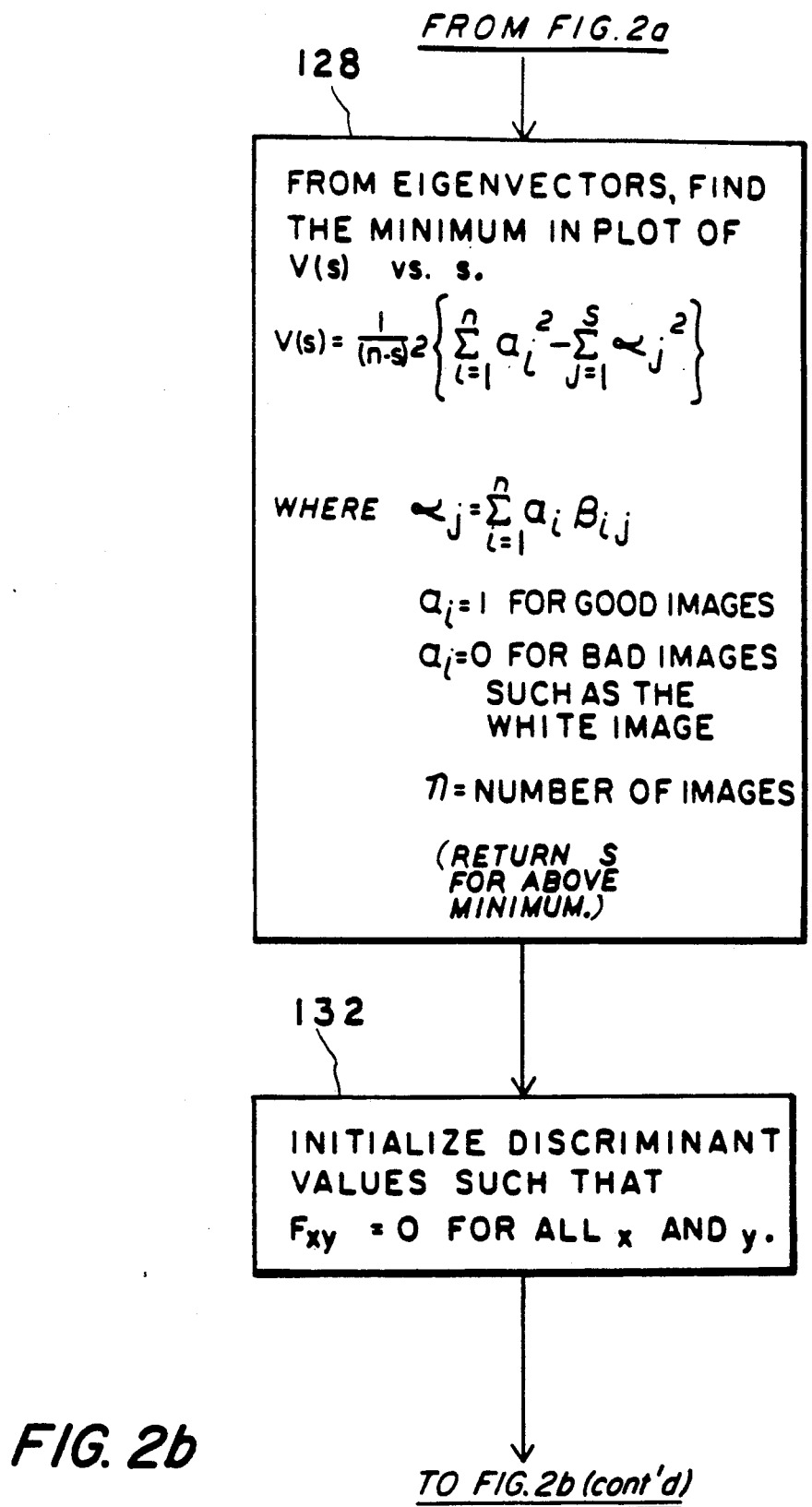
Figure 2B:
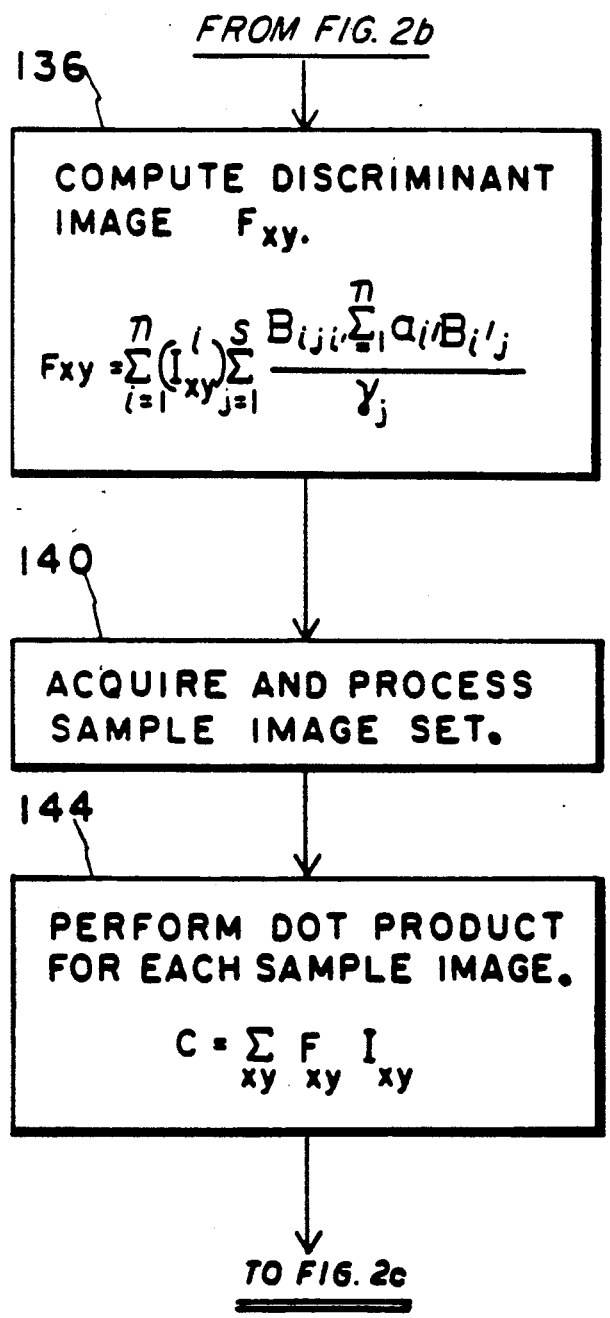

The method of this invention, which is largely carried out by elements 26 and 26A (preferably in accordance with the flow chart shown in FIG. 2), involves preprocessing a statistically significant number (e.g., 100 or 200) of images of products that are known to be acceptable (so-called "training products" or "training images") in order to enable processor 26 to construct a discriminant image for use in subsequent processing of products whose acceptability is unknown and therefore to be determined. Although the training images could be generated or acquired in any of a number of ways, the simplest method is generally to operate apparatus 10 with the desired number of training products 12. During processing of the training products, conveyor branch 20B is preferably locked in either one of its two positions. FIG. 2 will now be described.

Figure 3A:
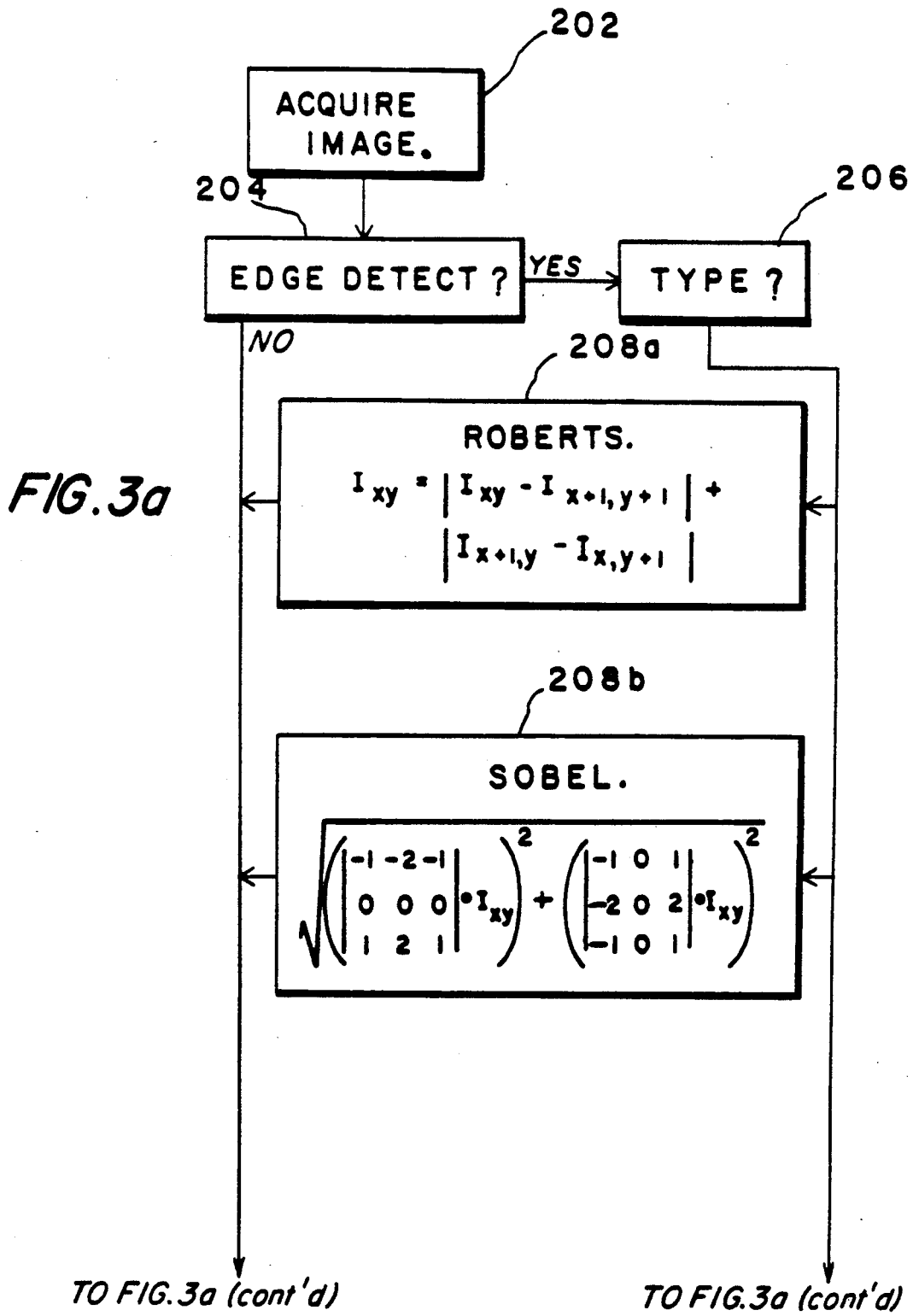
FIGS. 3a and 3b (referred to collectively as FIG. 3) are a more detailed flow chart of portions of the flow chart of FIG. 2.

In step 102 processor 26 initializes various program constants and reads various program control inputs (e.g., from an associated keyboard (not shown)), as is conventionally done at the start of a computer program. In step 104 processor 26 uses camera 24 and imaging hardware 26A to acquire a set of training images exactly as described above in connection with FIG. 1. Imaging hardware 26A digitizes the typically analog output signal information of camera 24 to produce a digitized version of the training image. For example, imaging hardware 26A may break the image down into a grid of 256 by 256 pixels and assign a digital value (proportional to brightness) to each pixel. (Although a 256 by 256 grid has been mentioned for purposes of illustration, any other grid size, proportions, or number of subdivisions could be used if desired. For greater resolution, for example, the grid could be 512 by 512 pixels. In any event, note that the number of training images employed is typically less than the number of pixels.) The resulting image data is variously referred to herein as I, $I_{xy}$, or I (and this same notation is used even after possible modification of the image data in such subsequent steps as the edge detection, centering and aligning, and binarizing steps described below). Each training image is processed as shown in FIG. 3, which will now be described.

Figure 5:
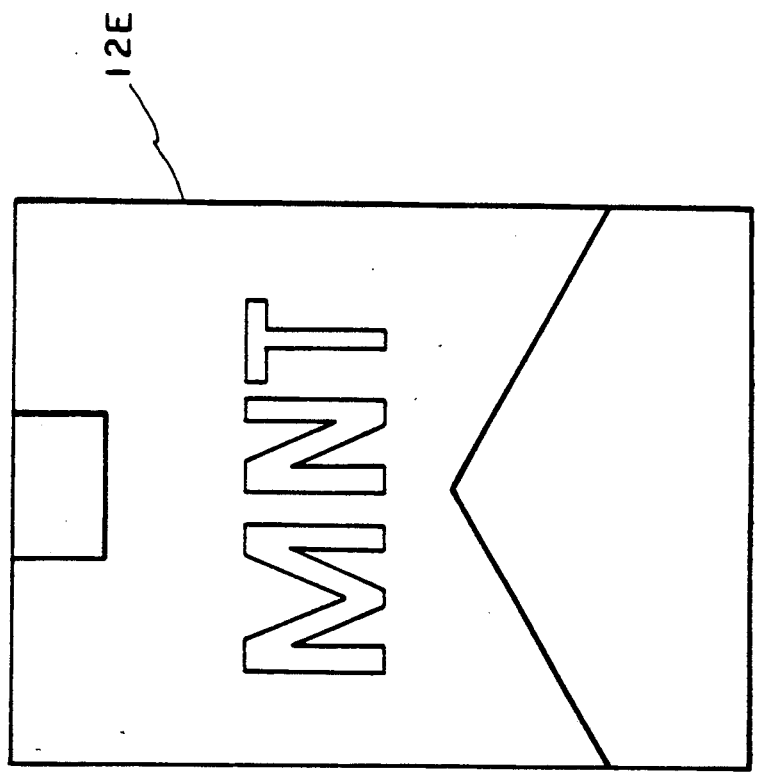
FIG. 5 is a view of the product image of FIG. 4 after partial processing in accordance with this invention.
Figure 4:
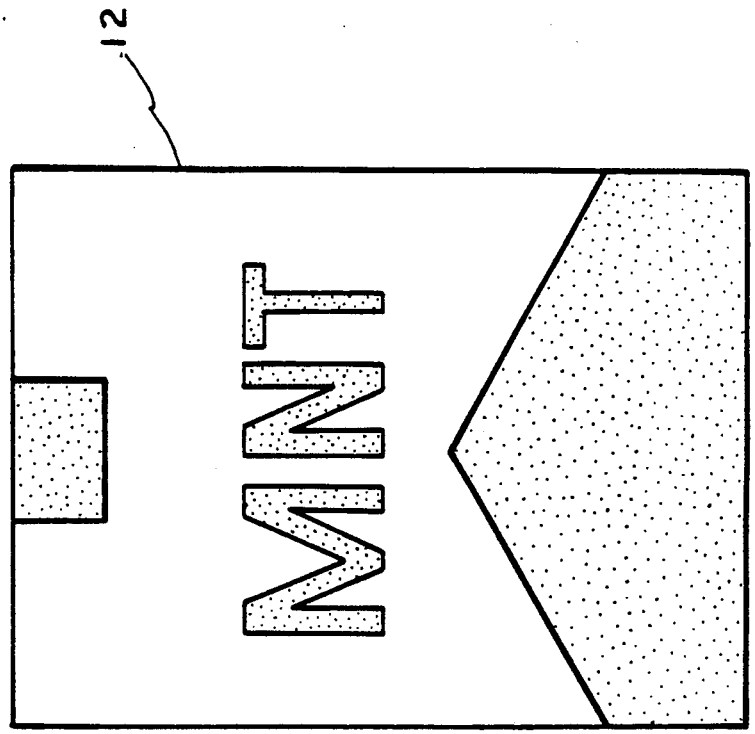
FIG. 4 is a view of a typical product image which can be processed in accordance with this invention.

Step 202 is merely a restatement of the portion of step 104 which relates to acquisition of an image. In step 204 one or more program control values (input in step 102) are tested to determine whether or not edge detection is to be performed. Edge detection is a well known technique which can be carried out in any of several different ways (see, for example, *Digital Image Processing* by Rafael C. Gonzalez, Addison-Wesley Publishing Company, 1987, pp. 331–41, and *Digital Image Processing* by William K. Pratt, John Wiley & Sons, Inc., 1978, pp. 478–92). In general, edge detection means that processor 26 alters the initial digital values of the pixels to produce output digital values such that pixels at or near significant changes in pixel value have output digital values which are relatively emphasized, while pixels which are not at or near significant changes in pixel value have output digital values which are relatively deemphasized. For example, FIG. 4 shows a typical image prior to performance of edge detection, while FIG. 5 shows the same image after edge detection. (Although only the meaningful portion of the image is shown in FIGS. 4 and 5, it will be understood that the image frame is typically larger than the product image.) As FIGS. 4 and 5 illustrate, pixels associated with transitions from bright to dark (i.e., "edges") in the input image (FIG. 4) tend to come out bright in the edge detected image (FIG. 5). (For convenience herein the "bright" portions of FIG. 5 are represented by the linework in that FIG.)

If edge detection is to be performed (as it is in the preferred embodiments), then step 206 is performed to identify the edge detection technique to be employed, again based on testing one or more program control values input in step 102. Although other edge detection techniques are known and may be employed if desired, four such techniques (described in the above-mentioned textbook by Pratt and respectively referred to herein as the "Roberts," "Sobel," "Laplacian," and "lowpass" techniques) are provided in alternative steps 208a-d in FIG. 3. For example, if the Roberts technique (step 208a) is selected, each output digital value $I_{xy}$ is given by the equation in box 208a in FIG. 3 (where x and y are the associated pixel coordinates, and the values to the right of the equal sign are the above-mentioned input digital values (prior to edge detection)). Alternatively, if any of the Sobel, Laplacian, or lowpass edge detection techniques are selected in step 206, then the output digital values are computed using the relationship shown in the corresponding box 208 in FIG. 3.

After edge detection (if any) as described above, control passes to step 220 where the THRESHOLD constant (established in step 102) is tested to determine whether or not it is 0. If the THRESHOLD constant is not 0, binarization of the image data has been requested. If so, control passes to step 222 in which each image data value which is greater than the THRESHOLD value is set equal to 1, and all other image data values are set equal to 0 as shown by the relationships in box 222 in FIG. 3. Note that FIG. 5 is the result of both edge detection and binarization. Binarization is performed in the preferred embodiments because it greatly increases the speed with which the data can be further processed and because it reduces the sensitivity of the process to variations in light level. I0 After binarization (if any) as described above, control passes to step 230 in which the "first moments" of the image are computed (using the equations in box 230 in FIG. 3) in order to make it possible to subsequently center and align successive images with one another. In these equations K and L are pixel coordinate indexes (like x and y in the preceding equations.) Accordingly, these equations compute the coordinates K' and L' of a reference point in each image which is substantially the same for all images. The data for each image can then be aligned with the data for all other images by shifting the data for each image (after the first image) so that the reference point for each image after the first image coincides with the reference point of the first image. (It may not be necessary to actually shift the image data to align the images. Rather, it may be sufficient to merely take into account the computed misalignment when further processing the data for each image.

Figure 6:
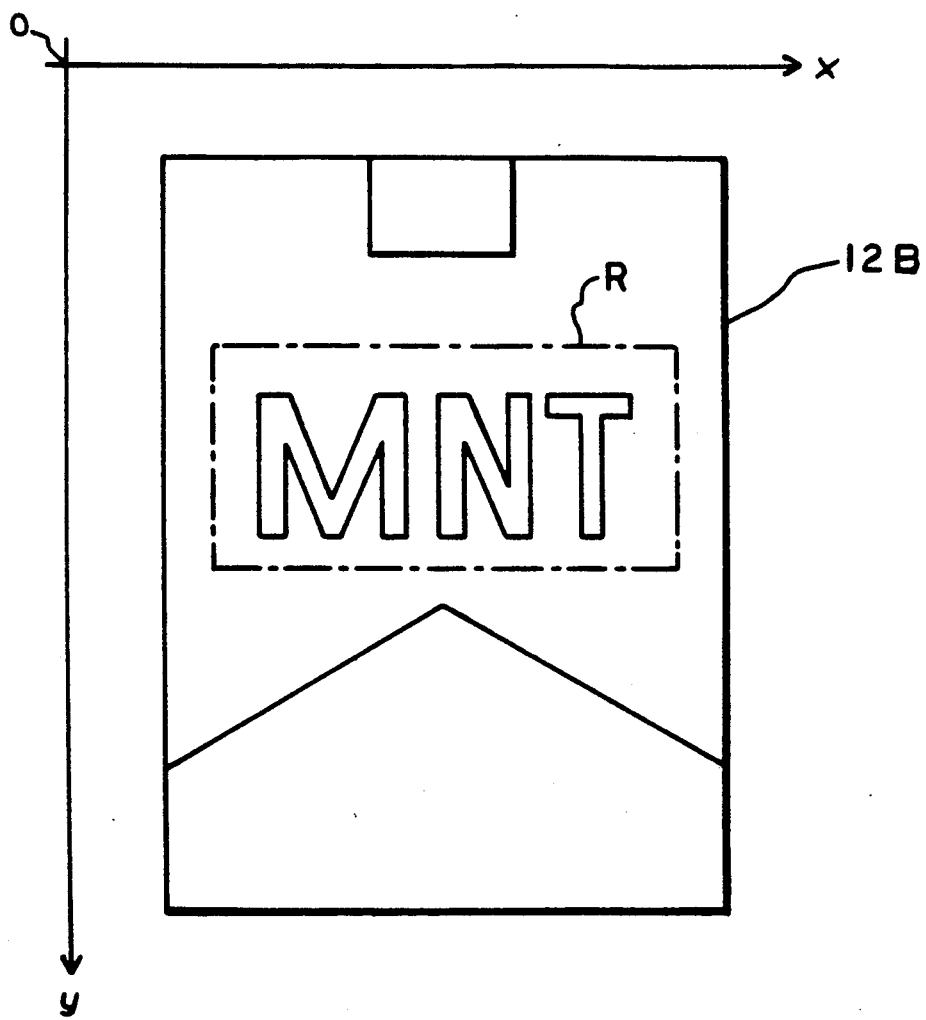
FIG. 6 is a view similar to FIG. 5 illustrating the manner in which the product image may be further processed in accordance with this invention.

Note that K and L need not span the entire image if there is some informative portion of the image which is relatively isolated from other significant portions of the image. For example, the region bounded by the chain-dotted line R in FIG. 6 might be selected as the domain of K and L if it were known that the binarized training image 12B could never move so much relative to that region that any of the letters "MNT" or any of the other image detail would cross the boundary of that region.

In step 230 the computation of variable a can be facilitated by having processor 26 form the logical AND of data like that depicted in FIGS. 7 and 8. FIG. 7 is a frame of data in which all rows are the same and in which each pixel position contains the value x of that pixel position. FIG. 8 is a frame of data in which all entries outside the region R are 0, while the actual binarized image data is preserved within the region R. (FIG. 8 includes greatly simplified, purely hypothetical image data.) The variable a results from forming the logical AND of the FIG. 7 and FIG. 8 data and then summing all of the resulting data.

Computation of the variable b in step 230 can be facilitated by having processor 26 form the logical AND of the data depicted in FIG. 9 and the data depicted in FIG. 8. FIG. 9 is a frame of data in which all columns are the same and in which each pixel position contains the y coordinate of that pixel position. The variable b results from forming the logical AND of the FIG. 9 and FIG. 8 data and then summing all of the resulting data.

Computation of the variable c in step 230 can be facilitated by having processor 26 form the logical AND of the data depicted in FIG. 8 and FIG. 10. FIG. 10 is a frame of data which is 0 everywhere outside of region R and 1 everywhere inside of region R. The variable c results from formin9 the logical AND of the FIG. 10 and FIG. 8 data and then summing all of the resulting data.

Figure 3B:
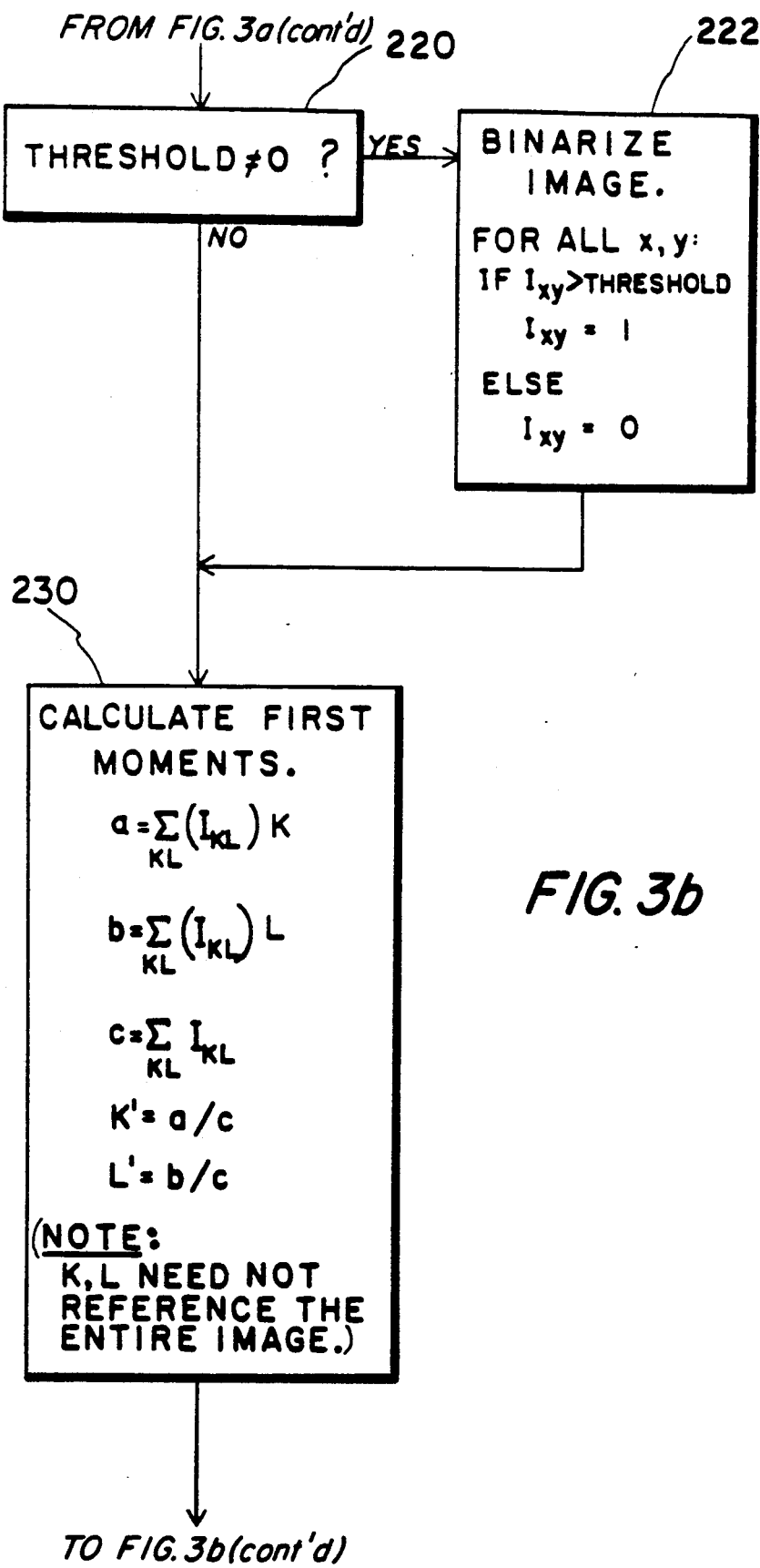
Figure 3B:
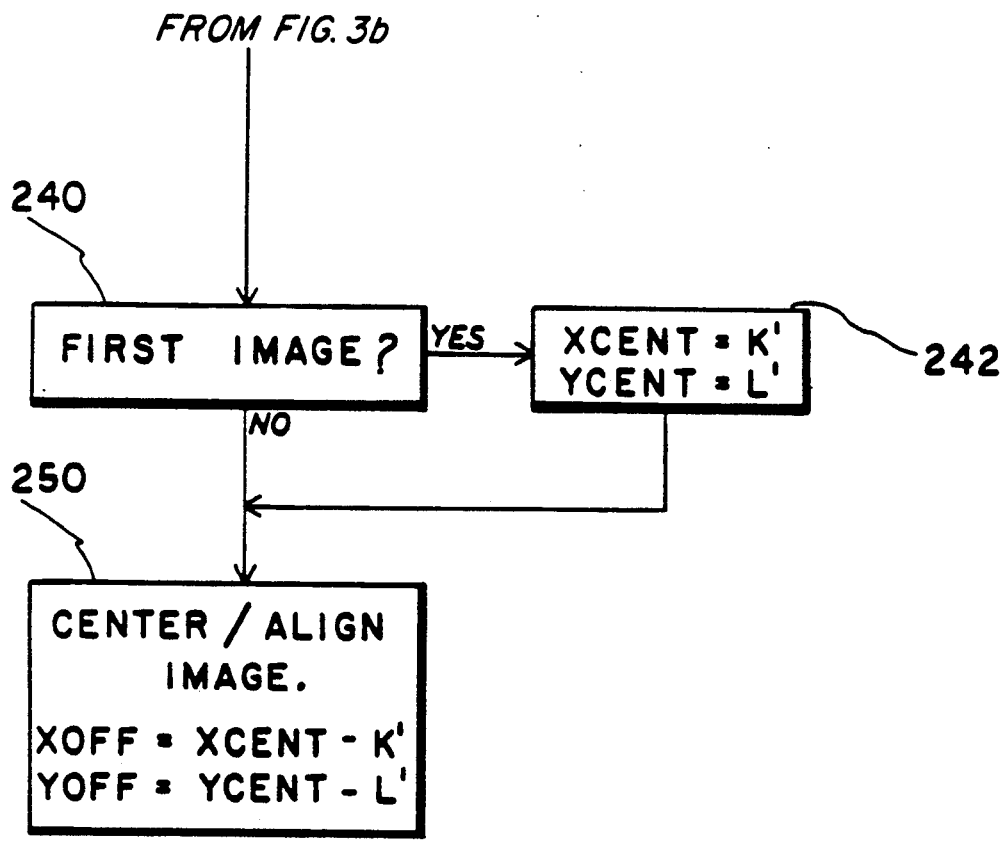

Continuing with FIG. 3b, after performing step 230, step 240 determines whether the image being processed is the first image. If so, step 242 is performed to set the variables XCENT and YCENT equal to the just-computed values of K' and L', respectively, and control then passes to step 250. Otherwise control passes directly to step 250.

In step 250 the image data is shifted (if necessary) to align each subsequent image with the first image. This is done by superimposing the reference point at coordinates K' and L' for each subsequent image on the location of that point for the first image. The amount by which each image must be shifted is therefore given by the variables XOFF and YOFF, computed using the equations in step 250 in FIG. 3. All of the data for the image is therefore shifted by the amounts XOFF and YOFF as part of step 250. (Again, it may not be necessary to actually shift the image data as long as the values XOFF and YOFF are taken into account when further processing that data.)

Returning now to FIG. 2, after the steps of FIG. 3 have been performed for all of the training images, control passes to step 110. In step 110, if requested via one or more inputs read in step 102, a "white image" (e.g., all ones) is added to the image list. Although this step is not indispensible, the efficacy of the discriminant image F (to be used in the actual inspection of products and computed as described in detail below) can be improved by adding such a known "bad" image to the training image set.

In step 120 the dot product of the data for every possible image pair (including the "white image," if any) is computed (as shown by the equation in box 120 in FIG. 2), and the resulting dot product values are used as the entries in dot product matrix A.

In step 124 eigenvalues $\gamma_j$ and eigenvectors $B_{ij}$ are calculated from the dot product matrix A. In particular, given $\underline{A}$ (a real, symmetric matrix), the matrices $\underline{A}$ and $\underline{\underline{G}}$ are obtained by solving the equation $\underline{AB} = \underline{BG}$ such that $\underline{BB}^+ = \underline{B}^+\underline{B} = \underline{1}$, where 1 is matrix of the form shown in FIG. 11. Note that $(\underline{B}^+)_{ij} = B_{ji}$ and the eigenvalues $\gamma_i$ are the diagonal elements of $\underline{\underline{G}}$, which is a matrix of the form shown in FIG. 12. Standard routines are available for solving these equations. See, for example, the IMSL, Inc. *Math Library* available from IMSL, Inc. of 2500 CityWest Boulevard, Houston, Tex. 77042-3020.

Step 128 is performed to determine the optimum amount of image information to be used in constructing the discriminant image F. This step is important because it reduces the sensitivity of the method to "noise" in the training images. If the discriminant image is calculated without performing this step, the effectiveness of the discriminant tends at first to improve as the number of training images increases, but to then degrade with further increases in the number of training images. Such degradation begins when redundancies in the training image set become significant (an effect which is difficult to predict). This problem is avoided by performing step 128.

Assuming a sufficient number of training images, the optimum discriminant image F generally results from using less than all of the available image information in the computation of the discriminant. Step 128 provides a simple procedure for reliably determining the point at which to truncate the image information used in the calculation of F.

Step 128 involves the computation of V as a function of s (an integer index variable which ranges from 1 to n, where n is the number of images in the training set). The equation for V is given in box 128 in FIG. 2. The value of s which gives the minimum value of V is determined as a result of the performance of step 128 and is used as described below in the performance of the subsequent steps.

In step 132 the discriminant image F (which is a two-dimensional matrix commensurate in size with the matrix of data for any actual image I) is initialized to 0. Then in step 136 the actual discriminant image values are computed using the equation in box 136 in FIG. 2. Note that the index j in this equation is truncated using the value of s returned after the performance of step 128. The discriminant image F computed in step 136 is therefore the optimum such image as explained above.

After the performance of step 136, processor 26 begins the performance of steps for determining an acceptance threshold or range to be used in conjunction with the discriminant image in the actual optical inspection process. In step 140 a statistically significant number (e.g., 50) of further training images (sometimes referred to herein as sample images to distinguish them from the training images processed in step 104) is acquired and processed as shown in FIG. 3. It is desirable for the sample images to be good images representative of the range of product images that will be encountered during the actual product inspection process. It is also desirable to know the standard deviation among good images so that a threshold value can be selected (in step 148 discussed below) that will result in false rejection of less than a given fraction of acceptable units.

In step 144 processor 26 computes the dot product of the discriminant image F and each sample image I using the equation in box 144 in FIG. 2. If the sample image is an acceptable image, the resulting value of C will be 1 or close to 1 (the value of $a_i$ used for good images in step 128). The more unacceptable the image, the farther C will be from 1.

After step 144 has been performed for each sample image, processor 26 performs step 148 in which the values of C for all of the sample images are processed using conventional techniques to compute their average ($C_{av}$) and the standard deviation $\sigma$ of their distribution. Thereafter, processor 26 computes threshold values $C_{th}$ equal to $C_{av}$ plus or minus a predetermined number of multiples of $\sigma$. For example, if the objective of the optical inspection process is to erroneously reject no more than about one acceptable product in 1000, then the values of $C_{th}$ are given by the equation in box 148 in FIG. 2 (a Gaussian distribution being assumed).

The apparatus of the invention is now ready to perform actual product inspections in accordance with the further steps shown in FIG. 2. In step 152 the image of a product to be inspected is acquired and processed as shown in detail in FIG. 3 and described above. In step 156 processor 26 computes the dot product D of the discriminant image $\overline{F}$ and the product image data I using the equation shown in box 156 in FIG. 2. As in the case of step 144, D will be 1 or close to 1 if the product has an acceptable image. D will be farther from 1 the more unacceptable the product image is.

In step 160 processor 26 compares D to the acceptance range determined in step 148. If D is between the upper and lower limits of the acceptance range, processor 26 performs step 164a to accept the product (i.e., by controlling conveyor branch 20B to convey the product to conveyor segment 20A). On the other hand, if D is outside the range bounded by the upper and lower limits of the acceptance range, processor 26 performs step 164b to reject the product (i.e., by controlling conveyor branch 20B to convey the product to conveyor segment 20R). Steps 152-164 are performed for each product 12 to be inspected.

The following additional information may be helpful in understanding the principles underlying the invention as described above. In general, the object is to compute a discriminant image F such that the following relationships are satisfied:

$$\sum_{xy} F_{xy} I_{xy} \cong 1 \quad \text{for all "good"} \quad (1)$$
$$\text{training images}$$

$$\sum_{xy} F_{xy}^2 \cong \text{minimum} \quad (2)$$

The number 1 in Equation (1) is merely an arbitrary, preferably nonzero, constant associated with a "good" or "acceptable" image.

If desired, the efficacy of the discriminant image can be improved by additionally requiring the following relationship to be satisfied:

$$\sum_{xy} F_{xy} \cong 0 \quad (3)$$

This requirement corresponds to the inclusion of the above-mentioned "white image" in the data set. The number 0 in Equation (3) is a constant associated with a "bad" or "unacceptable" image.

The efficacy of the discriminant image can be still further improved, if desired, by processing one or more images that are known to be unacceptable and making the discriminant image additionally satisfy the following relationship for each unacceptable image $I^u$ $$\sum_{xy} F_{xy} I_{xy}^u \cong 0 \quad (4)$$

The solution of Equations (1) and (2) (together with Equation (3) and/or (4) if desired) is simplified by constructing the discriminant image from a set of orthogonal images or "eigenimages" $\underline{\Phi}(1)$, where $$\underline{\Phi}^{(j)} = \sum_{i=1}^{n} \underline{I}^{(i)} B_{ij} \quad (5)$$

In Equation (5) n is the total number of training images (including any "white image" and any unacceptable images $I^u$), i is a training image index, and j is an eigenimage index. Indexes i and j both run from 1 to n.

The transformation matrix $\underline{B}$ in Equation (5) is orthogonal. That is $$\underline{B} \cdot \underline{B}^+ = \underline{B}^+ \cdot \underline{B} = \underline{1} \quad (6)$$

and $$\underline{\Phi}^i \cdot \underline{\Phi}^j = G_{ij} = \gamma_i \delta_{ij} \quad (7)$$

It follows that:

$$\underline{AB} = \underline{BG} \quad (8)$$

where $A_{ij} = \underline{I}^{(i)} \cdot \underline{I}^{(j)}$ as in step 120 of FIG. 2. Thus the columns of the transformation matrix $\underline{B}$ are simply the eigenvectors of the matrix $\underline{A}$.

The discriminant image $\overline{F}$ is formed from a truncated linear combination of the eigenimages defined above as follows:

$$\underline{F} = \sum_{j=1}^{s} C_j \underline{\Phi}^{(j)} \quad (9)$$

where it is assumed that the eigenimages are ordered such that $\gamma_1 > \gamma_2 > \ldots > \gamma_n$. (C in these equations is unrelated to C in steps 144, 148, and 160.) The series is truncated at $s<n$ functions in order to avoid the incorporation of noise in the discriminant image.

A unique feature of the approach presented here is the method for choosing s. The method of generalized cross-validation is used (see G. H. Golub et al., "Generalized Cross-Validation as a Method for Choosing a Good Ridge Parameter," *Technometrics*, Vol. 21, No. 2, 1979), but the orthogonal transformation introduced above greatly simplifies the implementation of this method. The truncation level s is chosen to be the value for which $$V(s) = \frac{1}{(n-s)^2}\left(\sum_{i=1}^{n} a_i^2 - \sum_{j=1}^{s}\left[\sum_{i=1}^{n} a_i B_{ij}\right]^2\right) \quad (10)$$

is a minimum. This is the determination made in step 128 in FIG. 2, and as in step 128 $a_i$ here is 1 for good images and 0 for the "white" or any other bad image. Having chosen s, the coefficients $C_j$ for Equation (9) are chosen so that $$W = \sum_i [\underline{F} \cdot \underline{I}^{(i)} - a_i]^2 \quad (11)$$

is a minimum. It follows that $$C_j = \frac{1}{\gamma_j} \sum_{i=1}^{n} a_i B_{ij} \quad (12)$$

Therefore, $$\underline{F} = \sum_{j=1}^{s} \frac{1}{\gamma_j}\left[\sum_{i=1}^{n} a_i B_{ij}\right]\underline{\Phi}^{(j)} \quad (13)$$

which corresponds to the computation performed in step 136 in FIG. 2

The foregoing method for determining the discriminant image $\underline{F}$ is unique in that the discriminant function is expressed as a linear combination of eigenimages with the series truncated at s terms. The effect of this truncation is to reduce the sensitivity of the method to noise in the training images. As has been mentioned, if the discriminant image is calculated without this truncation, the effectiveness of the discriminant at first improves as the number of training images increases, but then begins to degrade with the addition of further training images. Such degradation begins when redundancies in the training set become significant (an effect which is hard to predict). This problem is avoided in the method set forth above by truncating the eigenimage series at s images. Moreover, the present method includes a simple procedure for reliably determining the optimum value for s.

It will be noted that the systems of this invention effectively train themselves to deal with each new product inspection task. Each time a different product is to be inspected, the training portion of the invention (steps 102–148) is performed to allow the system to acquire the information needed to establish appropriate inspection criteria. The systems of this invention are therefore of universal application and do not require extensive set-up by a highly skilled operator. Note also that the systems of this invention advantageously inspect the entire image of a product, not just predetermined portions of such images.

B. Construction of the Discriminant Image From Bipolar Image Information

In the basic system described above, the discriminant image F is determined such that $$d_i = \sum_{xy} F_{xy} I_{xy}^{(i)} \quad (14)$$

where $\underline{I}^{(i)}$ is the ith training image and the dot product $d_i$ is approximately equal to 1 for a good image and much less than 1 (approximately 0) for an unacceptable image. In the basic system, F is constructed from a linear combination of training images which have been centered and, preferably, binarized. When binarized images containing zeros and ones are used, the discriminant image has zero or nearly zero values wherever the training images are consistently zero. In these regions the discriminant image is effectively blind, i.e., it is unable to recognize the improper appearance of a one in a region of a product image where the value should be 0. The addition of the above-described "white image" to the training image set partly overcomes this possible deficiency. However, a better approach may be to use bipolar rather than 0 and 1 binary training image data to construct the discriminant image F. In bipolar image data the entries are $-1$ and 1 rather than 0 and 1 as is assumed in the basic system.

Assuming that the image data $\underline{I}^{(i)}$ continues to be supplied in 0 and 1 binary form (as may be most convenient for most imaging and processing hardware), but that the discriminant image is to be constructed as though that image data were bipolar, the discriminant image should be such that the following relationships are satisfied:

$$[2\underline{I}^{(i)} - \underline{1}] \cdot \underline{F} = 1 \quad \text{for all good images} \quad (15a)$$
$$\ll 1 \quad \text{for all bad images} \quad (15b)$$

where $\underline{1}$ is an image in which all entries are equal to 1. Note that if $\underline{I}^{(i)}$ is 0 and 1 binary as is assumed above, $[2\underline{I}^{(i)} - \underline{1}]$ is bipolar. Let $$A_{ib} = [2\underline{I}^{(i)} - \underline{1}] \cdot [2\underline{I}^{(j)} - \underline{1}] \quad (16)$$

As in the basic system, $\underline{A}$ is diagonalized to obtain $\underline{G}$ and $\underline{B}$ such that $$\underline{G} = \underline{B}^+ \underline{A}\underline{B} \quad (17)$$

and $$G_{ij} = \gamma \text{hd } i\delta_{ij} \quad (18)$$

As in the basic system, the eigenimages $\underline{\Phi}^{(j)}$ are constructed such that $$\underline{\Phi}^{(j)} = \sum_{i=1}^{n} [2\underline{I}^{(i)} - \underline{1}]B_{ij} \quad (19)$$

It follows that the discriminant image $\underline{F}$ is given by Equation (9) where the values of $C_j$ are given by Equation (12). The lruncation level s is chosen to be the value for which $$V(s) = \frac{n}{(n-s)^2}\left(n - \sum_{j=1}^{s}\left[\sum_{i=1}^{n} B_{ij}\right]^2\right) \quad (20)$$

is a minimum (all ai being assumed to be 1 for this case). F has been construoted in accordance with Equation (14), which can be rewritten $$\underline{I}^{(i)} \cdot \underline{F} = [1 + \underline{1} \cdot \underline{F}]/2 \quad (21)$$

Therefore, for all good images, we should have $$\underline{I}^{(i)} \cdot \underline{F} p \quad (22)$$

where $$p = [1 + \underline{1} \cdot \underline{F}]/2 \quad (23)$$

which is just a constant number. Accordingly, it is not necessary to convert the data for the images of products being inspected from 0 and 1 binary form to bipolar binary form as long as the dot product of that data and F is compared to p (as in Equation (22)) rather than to 1 (as in the basic system). In other words, with reference to step 160 in FIG. 2, the product is accepted (step 164a) if the above-mentioned dot product is within a predetermined number of standard deviations of p. Otherwise, the product is rejected (step 164b).

As an alternative to using Equations (14)-(23), the same results can be achieved using the equations described above in connection with the basic system but with truly bipolar data for both the training images and the actual product images. As has been mentioned, however, this may require substantial amounts of data conversion (e.g., from 0 and 1 binary form to −1 and 1 bipolar binary form), and may therefore be less desirable than processing 0 and 1 data using Equations (14)-(23) in order to effectively render the data bipolar.

C. A More Accurate Centering Technique

The centering technique described above in connection with the basic system is based on locating the "center of mass" (x',y') of a region of interest. In particular, $$x' = \frac{\sum_{xy} I_{xy} x}{\sum_{xy} I_{xy}} \quad (24)$$

and $$y' = \frac{\sum_{xy} I_{xy} y}{\sum_{xy} I_{xy}} \quad (25)$$

(Note that (x',y') here is the same as (K',L') in FIG. 3b.) The variables x' and y' are approximately linear in $I_{xy}$. The coefficients, however, are constant and do not take into account the nature of the images which are being centered. As a result, the centering performed in the basic system may sometimes be susceptible to error, particularly when a sufficiently wide border of zeroes around the region of interest does not exist. Also it may be desirable to be able to accommodate fairly large product image shifts, which may be due to the location of the product in the field of view of the camera and not to any defect in the product image. The following new centering technique incorporates training in order to take into account the nature of the image being centered. This centering technique therefore gives better results in many cases than the centering technique employed in the basic system.

The object of the new centering technique is to construct filters $\underline{F}^H$ and $\underline{F}^V$ such that $$\sum_{xy} F^H_{xy} I_{x-\delta H, y-\delta V} \approx \delta_H \quad (26)$$

and $$\sum_{xy} F^V_{xy} I_{x-\delta H, y-\delta V} \approx \delta_V \quad (27)$$

for a set of values $\delta_H$ and $\delta_V$ spanning the range of shifts expected during inspection. In Equations (26) and (27) $\underline{I}$ can be any one of the good images. It is convenient, and in fact preferable, to actually consider only a small subregion of the image. This approach is convenient because it reduces the computations required. This approach is preferable because the subregion chosen can be a region which is generally free of variation, thereby enhancing the performance of the method. The boundaries of this subregion are fixed in space. That is, the corners (assuming a rectangular subregion) correspond to specific pixels. Because calculation of the horizontal and vertical offset filters $\underline{F}^H$ and $\underline{F}^V$ is identical, it will be sufficient to describe the calculation of only the horizontal filter in detail.

$\underline{F}^H$ is constructed in a way that minimizes the quantity $$\sum_{xy} (F^H_{xy})^2 \quad (28)$$

The procedure is almost identical to the procedure used for construction of the discriminant image $\underline{F}$ in the basic system.

First, "eigenimages" are constructed from a set of m training images, where m is the number of shifts considered. For example, if shifts by 0, ±1, and ±2 pixels are expected in the horizontal direction, and shifts by 0 and ±1 pixels are expected in the vertical direction, m would be 5×3=15. Of course, it is not absolutely necessary to train on all possible shifts. If, for example, horizontal and vertical shifts by as many as ±10 pixels are expected, training might be done on horizontal and vertical shifts of 0, ±2, ±4, ±6, ±8, and ±10 pixels, which results in m=11×11=121.

As has been mentioned, the eigenimages are constructed from the set of m shifted images. This set of shifted images is referred to as $\underline{J}^{(k)}$ (where k=1, m) to distinguish these shifted images from the training images used to construct $\underline{F}$. Recall that $\underline{J}^{(k)}$ are each constructed by shifting a particular image $\underline{I}$, and the $\underline{J}^{(k)}$ may be subregions of the entire image. The eigenimages are defined by $$\underline{\Phi}^{(j)} = \sum_{i=1}^{m} \underline{J}^{(i)} B_{ij} \quad (29)$$

We require $$\underline{B} \cdot \underline{B}^{30} = \underline{B}^+ \cdot \underline{B} = 1 \quad (30)$$

where 1 is as shown in FIG. 11. We further require $$\underline{\Phi}^{(i)} \cdot \underline{\Phi}^{(j)} = G_{ij} = \gamma_i \delta_{ij} \quad (31)$$

It follows that $$\underline{A} \cdot \underline{B} = \underline{B} \cdot \underline{G} \quad (32)$$

where $$A_{ij} = f^{(i)} \cdot f^{(j)} \quad (33)$$

(Note that the quantities $\underline{A}$, $\underline{B}$, and $\underline{G}$ are different from those used to obtain the discriminant image $\underline{F}$.) We then construct $$\underline{F}^H = \sum_{j=1}^{s} C_j \underline{\Phi}^{(j)} \quad (34)$$

where $$\gamma_1 > \gamma_2 > \ldots > \gamma_m \text{ and } s \leq m \quad (35)$$

The variable s is chosen by minimizing $$V(s) = \frac{1}{(m-s)^2} \left( \sum_{i=1}^{m} (\delta_i^H)^2 - \sum_{j=1}^{s} \left[ \sum_{i=1}^{m} \delta_i^H B_{ij} \right]^2 \right) \quad (36)$$

where $\delta_i^H$ is the horizontal shift of the ith training image. The coefficient $C_j$ is chosen so that $$\sum_{i=1}^{s} [\underline{F}^H \cdot f^{(i)} - \delta_i^H]^2 \quad (37)$$

is a minimum. It follows that $$C_j = \frac{1}{\gamma_j} \sum_{i=1}^{m} \delta_i^H B_{ij} \quad (38)$$

Therefore $$\underline{F}^H = \sum_{j=1}^{s} \frac{1}{\gamma_j} \left[ \sum_{i=1}^{m} \delta_i^H B_{ij} \right] \underline{\Phi}^{(j)} \quad (39)$$

The filter $\underline{F}^V$ is constructed in a similar manner.

When $\underline{F}^H$ and $\underline{F}^V$ have been constructed as described above, the amount by which any product image is shifted can be determined (as in step 250 in FIG. 3) from the following equations:

$$XOFF = \underline{F}^H \cdot \underline{I} \quad (40)$$

$$YOFF = \underline{F}^V \cdot \underline{I} \quad (41)$$

D. Image Segmentation

The basic system involves the construction and use of a single discriminant image for classifying test images as acceptable or unacceptable. This approach may make it difficult or impossible to detect relatively small but highly unacceptable defects in areas which are not normally subject to much variation if there are other areas which are subject to substantial but acceptable variation. In the case of cigarette packages, for example, the tax stamp area may be subject to substantial variation due to acceptable fluctuations in the positioning of the tax stamp. This may dictate the sensitivity of the inspection method in such a way as to make it impossible to detect smudges or spots elsewhere on the package.

The performance of the inspection method can be dramatically improved in the foregoing respect if each image is divided into segments and discriminant images are independently constructed for each segment. The acceptance criteria (i.e., the upper and lower thresholds analogous to those in step 160 in FIG. 2) may be different for each segment, reflecting the different level of variation present in the various segments. An image is classified as unacceptable if the dot product of the discriminant image and the image data for any segment is outside the thresholds for that segment.

Another advantage of image segmentation is that it allows the system to identify which part or parts of any unacceptable image are faulty. This may help the operator of the system identify and correct the problem in the apparatus producing the products being inspected.

Figure 13B:
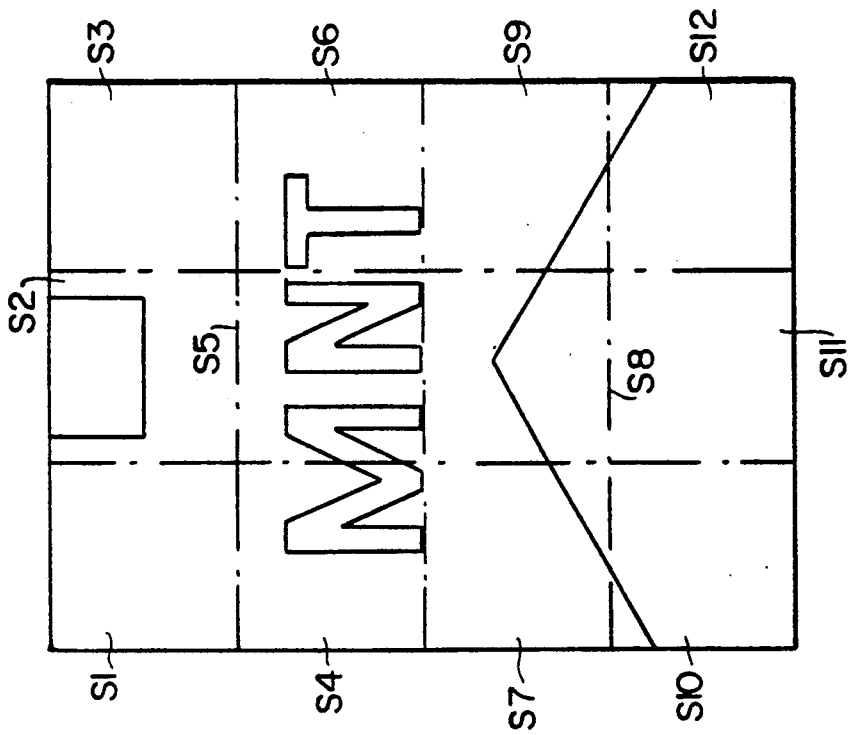
FIGS. 13a and 13b are views of the product image of FIG. 5 showing examples of how that image may be divided into segments for processing on a segment-by-segment basis.
Figure 13A:
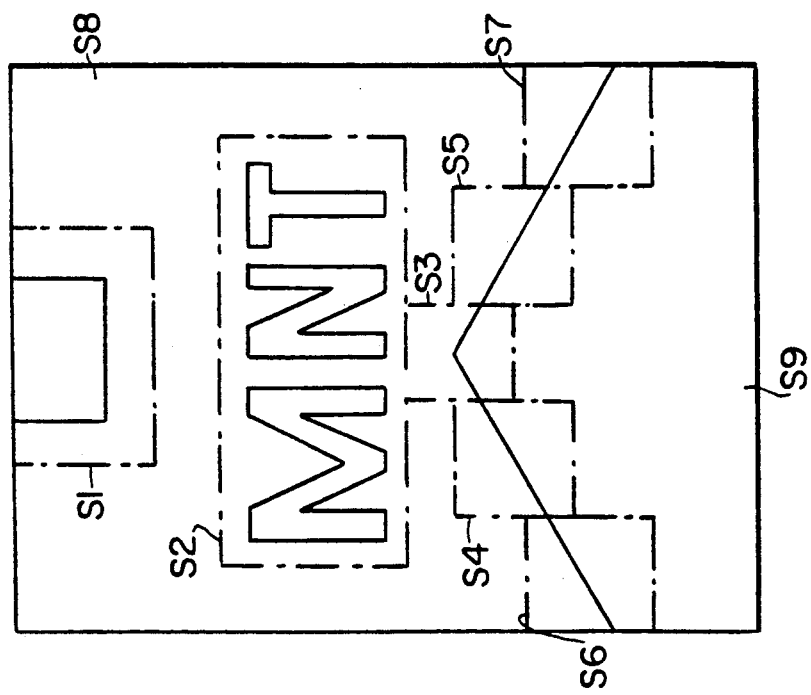

Images may be segmented either with the properties of the image taken into account (e.g., as in FIG. 13a) or substantially without regard for the properties of the image (e.g., as in FIG. 13b). In FIG. 13a, for example, the image is segmented so that the tax stamp falls in segment S1, the letters "MNT" fall in segment S2, the chevron line falls in segments S3–S7, the background above the chevron falls in segment S8, and the background below the chevron falls in segment S9. In FIG. 13b, on the other hand, the image is divided into 12 equally sized and uniformly distributed segments S1–S12.

E. Adaptive Training

In the basic system, the discriminant image F is fully constructed from a plurality of training images in advance of the processing of any of the products to be inspected. This batch training procedure may have disadvantages such as the following:

1. The processing time required to generate the discriminant image increases rapidly with increasing training set size. For example, it may not be convenient to consider more than about 250 training images.

2. The processing hardware needed for training may be different from that needed for inspection. This may add to the cost of the inspection system.

3. The apparatus must have the capacity for storing all the training images. This may also add to the cost of the system.

4. The discriminant image cannot be changed once the inspection is initiated. Slow, acceptable drift in the product being inspected is not taken into account.

The foregoing possible disadvantages of the training aspects of the basic system can be avoided by using an adaptive training mode analogous to the Widroff-Hoff training algorithm, which is known in signal processing but which, to the best of our knowledge, has not been used for the construction of a discriminant image. With this method, training of the system and inspection of products are done simultaneously as will now be described.

Initially, the discriminant image is taken as the first good image, properly normalized. In particular:

$$\underline{F}^{(1)} = \frac{f^{(1)}}{|f^{(1)}|} \quad (42)$$

where

-continued $$|I^{(1)}| = \left\{ \sum_{xy} (I^{(1)}_{xy})^2 \right\}^{\frac{1}{2}} \quad (43)$$

$I^{(1)}$ is the binary image data which has already been centered and possibly segmented. For each succeeding good image, the dot product of the discriminant image and the training image is calculated in order to obtain an error value $$e_i = 1 - \underline{F}^{(i-1)} \cdot \frac{I^{(1)}}{|I^{(1)}|} \quad (44)$$

If desired, $|I^{(i)}|$ in Equation (44) can be replaced by a constant value (e.g., the value computed in accordance with Equation (43)). The discriminant image is then updated as follows:

$$F^{(i)} = \underline{F}^{(i-1)} + \delta e_i \frac{I^{(i)}}{|I^{(i)}|} \quad (45)$$

where $\delta$ is a predetermined learning or adapting parameter, and where $|I^{(i)}|$ may again be replaced by a constant value as in Equation (44). The learning or adapting parameter $\delta$ determines how fast the discriminant image is updated. The method converges for values of $\delta$ between 0 and 2. If $\delta$ is more than 1, the system responds more rapidly to changes in successive images (so-called "over-correction"). If $\delta$ is less than 1, the system responds more slowly to changes in successive images (so-called "undercorrection").

After a sufficient number of images have been processed as described above to produce a relatively stable discriminant image, that image can be used exactly as described above in connection with the basic system to classify further images as acceptable or unacceptable. In particular, the dot product of the current discriminant image and the image to be classified is computed and compared to upper and lower threshold values. If the dot product is between those threshold values, the image is classified as acceptable. Otherwise the image is classified as unacceptable. At the same time, the discriminant image continues to be updated by each succeeding acceptable image in accordance with Equation (45).

If it is desired for the training and inspection modes to be sequential (as in the basic system) rather than simultaneous as described immediately above, the adaptive training method can still be used with an initial set of training images to obtain a discriminant image which thereafter remains fixed during actual product image classification. In this case, the available set of training images can best be utilized by applying the adaptive process to those images repeatedly (i.e., in an iterative manner) until convergence is obtained. Convergence is achieved when the rms (root mean square) error obtained for the images is below a specified tolerance. For example, we have found that with a training set of 200–300 images, convergence with an error of less than 0.001 can be obtained with ten iterations.

The adaptive training technique can be easily integrated into a production environment where minimum operator supervision is desired. Assuming that the first few images are good, the system can be quickly initiated and used for product testing while at the same time updating it after each good image is encountered. If the image is classified as unacceptable, the filter is not updated for that image. The threshold values are determined from the error statistics as in the batch processing case. The learning can be turned off at any time or, if it is desired to track slow acceptable drifts over time, allowed to continue during inspection.

F. Illustrative Enhanced System Embodiments

Figure 14A:
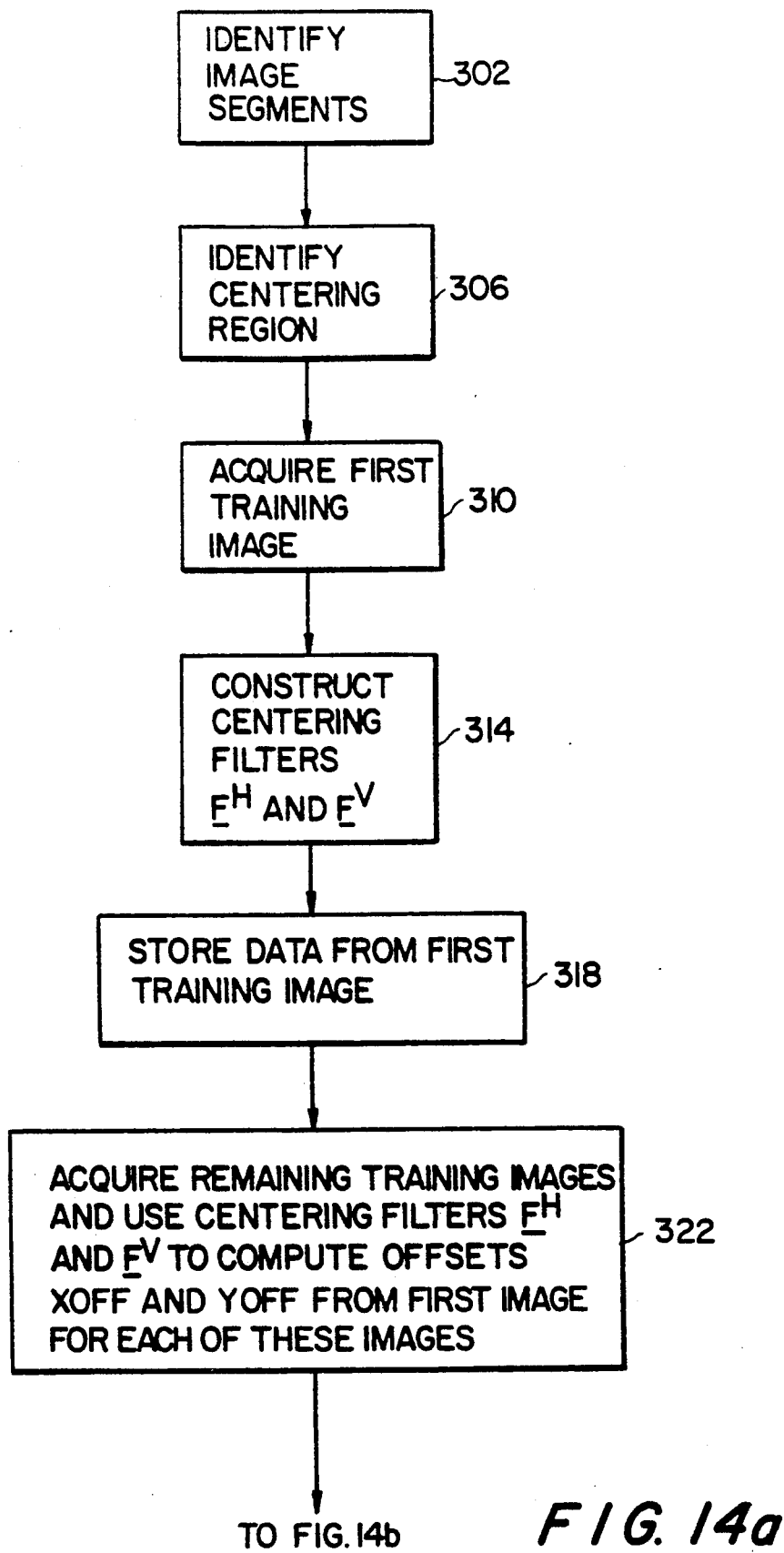
FIGS. 14a, 14b, and 14c (referred to collectively as FIG. 14) are a flow chart of an alternative embodiment of this invention having various enhancements.
Figure 14B:
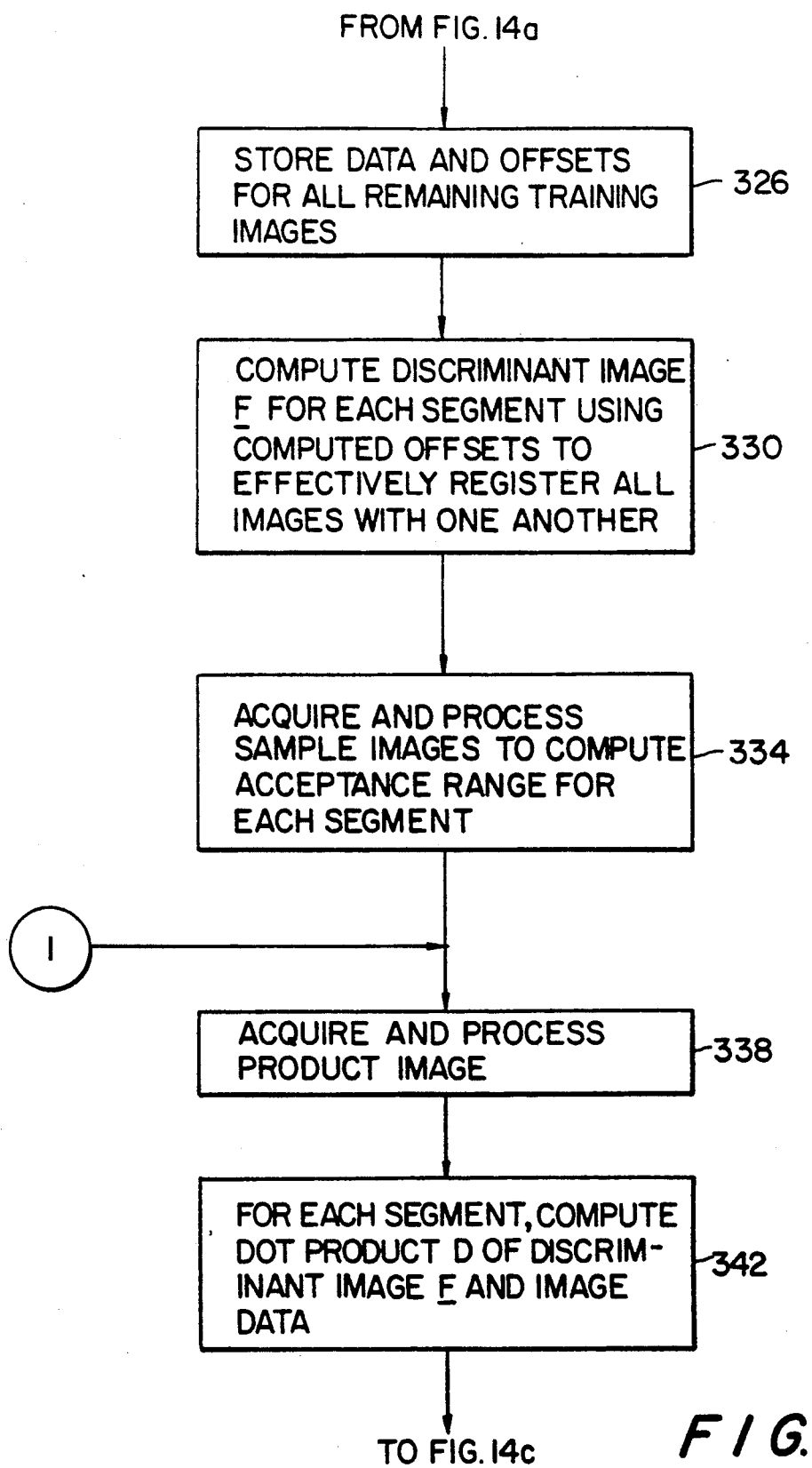
Figure 14C:
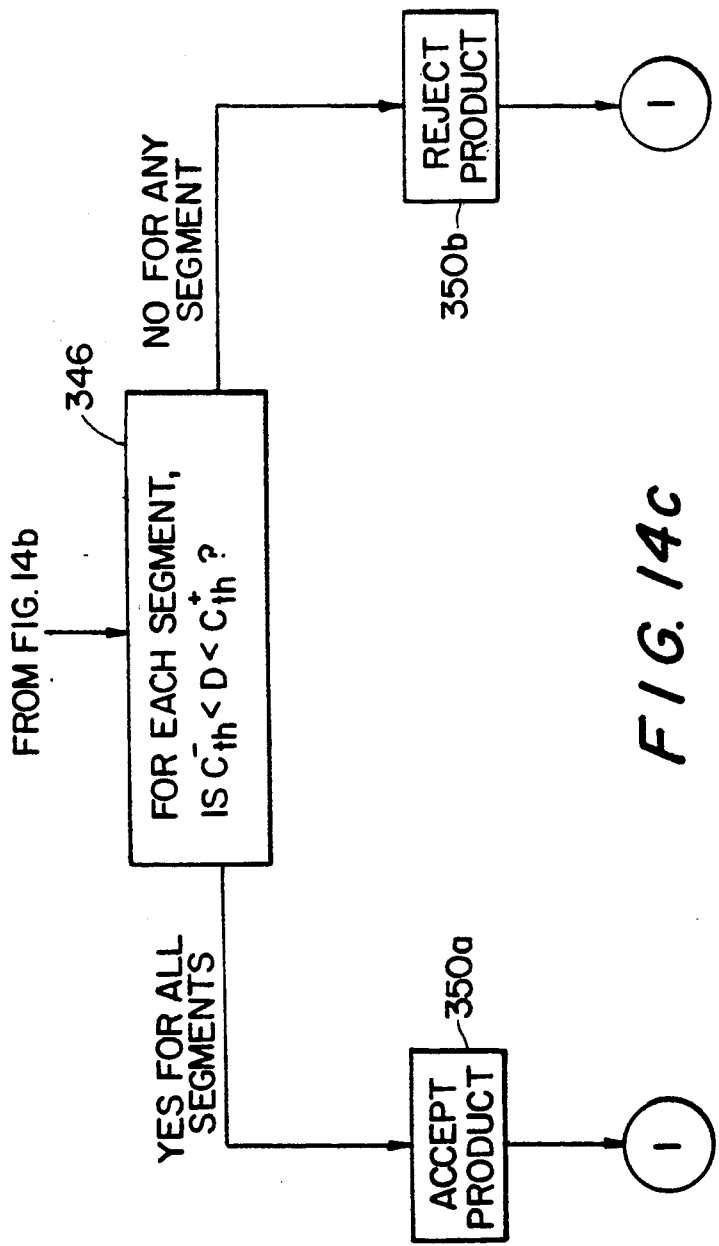

FIG. 14 is a flow chart of an illustrative system including the enhancements described in Sections B-D above. In other words, FIG. 14 illustrates an embodiment which includes (1) construction of the discriminant image from bipolar image information as described in Section B above, (2) use of the more accurate centering technique described in Section C above, and (3) image segmentation as described in Section D above. Although all three of these enhancements are included in the system of FIG. 14, it will be understood that these enhancements do not depend on one another, and that the system could include only one or two of these enhancements if desired.

In step 302 the image segments to be used are identified (e.g., as shown in FIG. 13a or FIG. 13b and as discussed in Section D above). In step 306 any convenient centering region is identified (as discussed in Section C above). In step 310 the first training image is acquired and digitized. This step is analogous to steps 202–222 in FIG. 3. The resulting image data can be either 0 and 1 binary (as is assumed in the basic system) or it can be bipolar binary (as discussed in Section B above). In step 314 the image data from step 310 is used to construct or compute centering filters $F^H$ and $F^V$ as in Section C above. In step 318 the image data for the first training image is stored for future reference.

In step 322 the remaining training images are acquired as in step 310, and the centering filters computed in step 314 are used to determine the amounts by which each of these further training images is offset from or out of registration with the first training image. In step 326 the image data and offsets for each of these further training images are stored.

In step 330 the image data for all of the training images and the offsets for all training images after the first one are used to compute a discriminant image F for each image segment. This step is generally similar to steps 120–136 in FIG. 2. If the training image data is in bipolar binary form, the equations shown in FIG. 2 and Section A above can be used to compute these discriminant images as explained in Section B above. Alternatively, if the training image data is in 0 and 1 binary form, then the modified equations provided in Section B above can be used to effectively convert that data to bipolar form In step 334 further "sample" images are acquired and processed in a manner generally similar to steps 140–148 in FIG. 2 to determine upper and lower acceptance limits $C_{th}^+$ and $C_{th}^-$ for each image segment. This step includes use of centering filters $F^H$ and $F^V$ to effectively register each sample image with the discriminant images. $C_{th}^+$ and $C_{th}^-$ may be related to 1 if the sample image data is in bipolar binary form, or they may be related to p from Equation (23) if the sample image data is in 0 and 1 binary form.

In step 338 a product image is acquired and processed in a manner analogous to step 152 in FIG. 2. Once again, this step includes using centering filters $F^H$ and $F^V$ to effectively register the product image. In step 342 the dot product D of the discriminant image for each segment and the product image data for that segment is formed in a manner analogous to step 156 in FIG. 2. Once again these dot product values may be similar to those in the basic system if the product image data is in bipolar binary form, or they may be related to p from Equation (23) if the product image data is in 0 and 1 binary form.

In step 346 the dot product for each segment is compared to the upper and lower acceptance thresholds for that segment. If the dot product for any segment is outside the acceptance thresholds for that segment, the product is rejected in step 350b. Otherwise the product is accepted in step 350a. The system then returns to step 338 to begin processing the next product image.

Figure 15A:
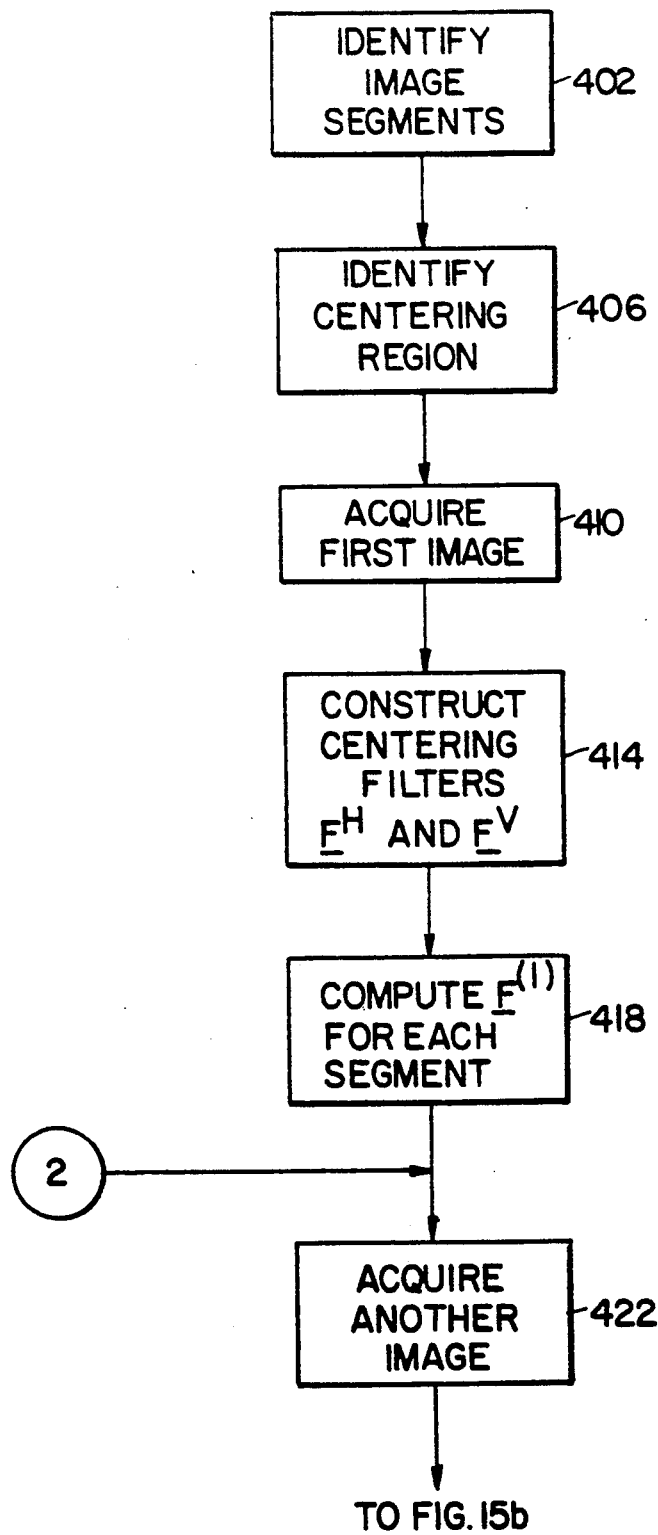
FIGS. 15a, 15b, and 15c (referred to collectively as FIG. 15) are a flow chart of an another alternative embodiment of this invention having another combination of enhancements.
Figure 15B:
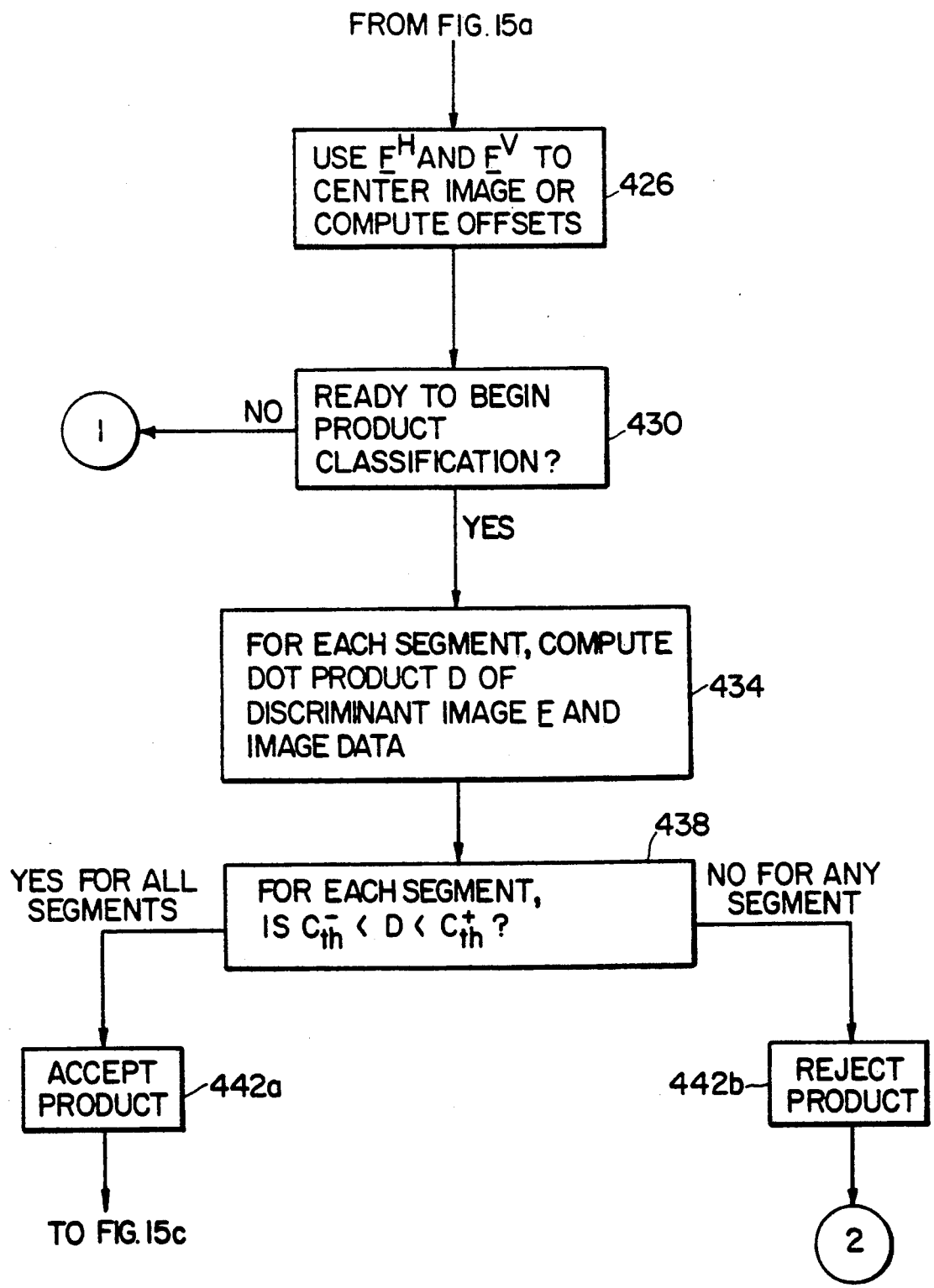
Figure 15C:
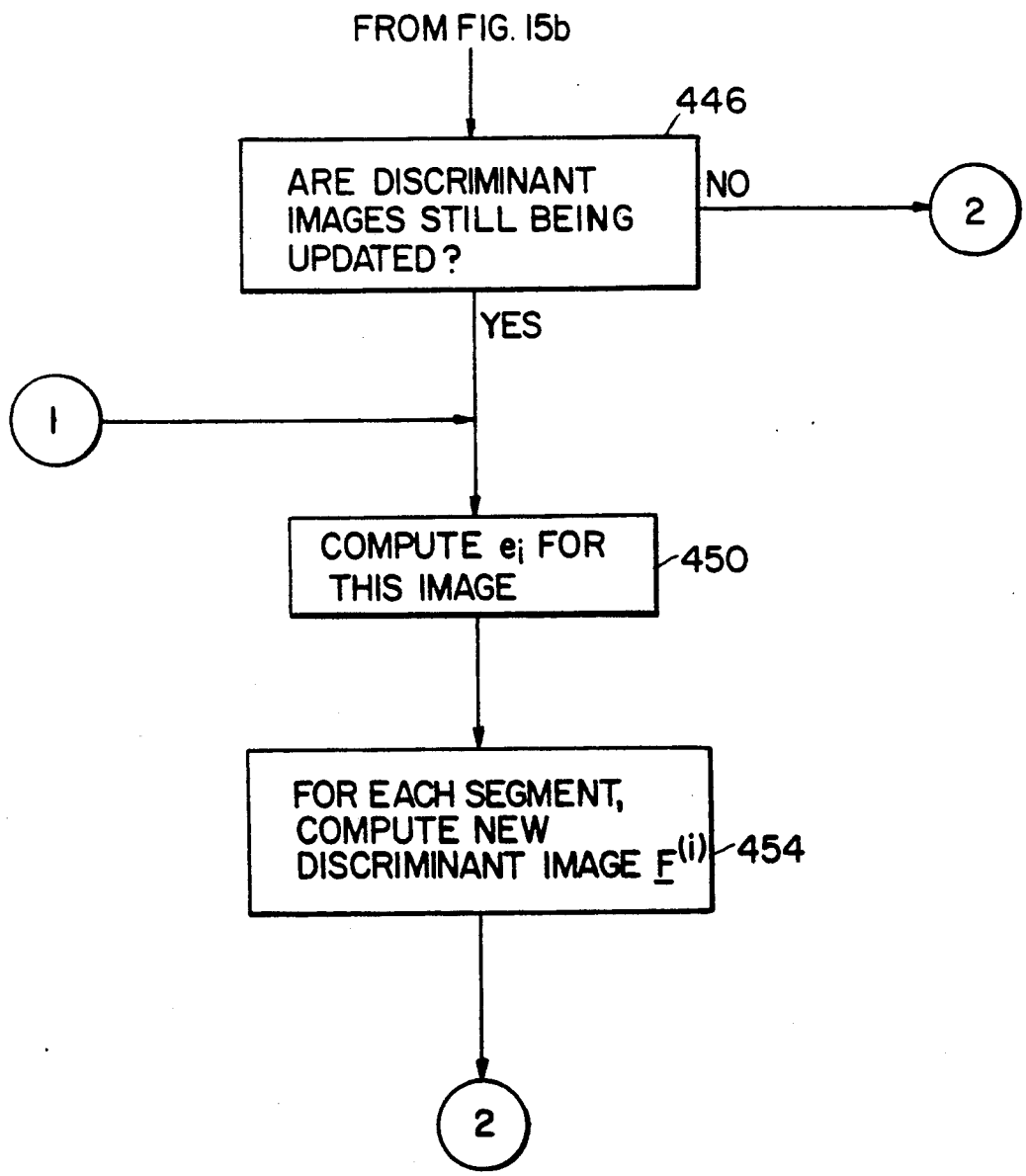

FIG. 15 is a flow chart of a system including the features discussed in Sections C-E above, and which may also include the feature discussed in Section B above. Again, these features do not depend on one another so that any one or more of them can be eliminated if desired. The most important difference between the system of FIG. 15 and the system of FIG. 14 is that the FIG. 15 system employs the adaptive training feature discussed in Section E above. Accordingly, that aspect of the FIG. 15 system will be considered in the greatest detail in the ensuing discussion.

Steps 402-414 are similar to steps 302-314 in FIG. 14 and therefore do not require further discussion here. In step 418 the initial discriminant image for each segment is computed as in Equation (42).

In step 422 the next image is acquired in the manner of step 410. In step 426 this next image is centered or effectively centered by computing its offsets from the first image as in Equations (40) and (41). In step 430, if the system is ready to begin classifying products as acceptable or unacceptable, control passes to step 434. Otherwise control passes to step 450. Steps 434-442 are similar to steps 342-350 in FIG. 14 and therefore require no further explanation. If the product is determined to be acceptable (step 442a), then step 446 is performed to cause control to pass to step 450 if the discriminant images are still being updated. Otherwise control returns to step 422 to begin processing of the next image. Control also returns to step 422 if (in step 422b) the product is determined to be unacceptable.

In step 450 (which may be reached either from step 430 or step 446) the value $e_i$ is computed as in Equation (44). In step 454 a new discriminant image is computed for each segment in accordance with Equation (45). Control then returns to step 422 to begin processing of the next image.

It will be understood that the foregoing is merely illustrative of the principles of the invention, and that various modifications can be made by those skilled in the art without departing from the scope and spirit of the invention. For example, although image frames of 256 by 256 pixels have been mentioned, other image frame sizes and shapes can be used if desired.

We claim:

1. The method of determining whether or not a surface of an object has substantially the same appearance as the corresponding surface of a plurality of training objects, said method comprising the steps of:

for each training object, (a) forming a two-dimensional image of said surface, (b) using computer processor means to subdivide said two-dimensional image into a plurality of pixels, (c) using computer processor means to digitize each of said pixels by associating with each pixel an output digital value proportional to an optical characteristic of the associated pixel, and (d) using said computer processor means to binarize each of said output digital values by associating a first binary value with each of said output digital values which is on one side of a first predetermined threshold value and by associating a second binary value with each of said output digital values which is on the other side of said first predetermined threshold value;

using said computer processor means to associate a discriminant value with each of said pixels, each discriminant value being chosen so that, for each training object, the dot product of the discimrnant values and the binary values is approximately a predetermined nonzero constant value;

repeating steps (a)-(d) for said object; and using said computer processor means to compare the dot product of said discriminant values and the binary values for said object to said predetermined nonzero constant value;

said first and second binary values and said predetermined nonzero constant value being selected so that the data resulting from step (d) for each training object and for said object is at least effectively rendered bipolar.

2. The method defined in claim 1 wherein said first and second binary values are −1 and 1.

3. The method defined in claim 1 wherein said first and second binary values are 0 and 1, and wherein said discriminant values are selected such that $$[2\underline{I}^{(i)}-\underline{1}]\cdot\underline{F}=1$$

for all acceptable images, and such that $$[2\underline{I}^{(i)}-\underline{1}]\cdot\underline{F}<<1$$

for all unacceptable images, where $\underline{I}^{(i)}$ is the data that results from step (d) for the ith training object, $\underline{1}$ is a matrix in which all entries are 1, and $\underline{F}$ is the matrix of all discriminant values.

4. The method defined in claim 3 wherein said predetermined nonzero constant value is the value p selected such that $$p=[1+\underline{1}\cdot\underline{F}]/2.$$

5. Apparatus for determining whether or not a surface of an object has substantially the same appearance as the corresponding surface of a plurality of training objects comprising:

means for, for each training object, (a) forming a two-dimensional image of said surface, (b) subdividing said two-dimensional image into a plurality of pixels, (c) digitizing each of said pixels by associating with each pixel an output digital value proportional to an optical characteristic of the associated pixel, and (d) binarizing each of said output digital values by associating a first binary value with each of said output digital values which is on one side of a first predetermined threshold value and by associating a second binary value with each of said output digital values which is on the other side of said first predetermined threshold value;

value with each of said pixels, each discriminant value being chosen so that, for each training object, the dot product of the discriminant values and the binary values is approximately a predetermined nonzero constant value;

means for repeating functions (a)–(d) with respect to said object; and means for comparing the dot product of said discriminant values and the binary values for said object to said predetermined nonzero constant value;

said first and second binary values and said predetermined nonzero constant value being selected so that the data resulting from function (d) for each training object and for said object is at least effectively rendered bipolar.

6. The apparatus defined in claim 5 wherein said first and second binary values are −1 and 1.

7. The apparatus defined in claim 5 wherein said first and second binary values are 0 and 1, and wherein said discriminant values are selected such that $$[2\underline{I}^{(i)} - \underline{1}] \cdot \underline{F} = 1$$

for all acceptable images, and such that $$[2\underline{I}^{(i)} - \underline{1}] \cdot \underline{F} \ll 1$$

for all unacceptable images, where $\underline{I}^{(i)}$ is the data that results from function (d) for the ith training object, $\underline{1}$ is a matrix in which all entires are 1, and $\underline{F}$ is the matrix of all discriminant values.

8. The apparatus defined in claim 7 wherein said predetermined nonzero constant value is the value p selected such that $$p = [1 + \underline{1} \cdot \underline{F}]/2.$$

9. The method of determining whether of not a surface of an object has substantially the same appearance as the corresponding surface of a plurality of training objects, said method comprsiing the steps of:

for each training object, (a) forming a two-dimensional image of said surface, (b) using computer processor means to subdivide said two-dimensional image into a plurality of pixels, (c) using said computer processor means to digitize each of said pixels by associating with each pixel an output digital value proportional to an optical characteristic of the associated pixel, and (d) using said computer processor means to binarize each of said output digital values by associating a first binary value with each of said output digital values which is on one side of a first predetermined threshold value and by associating a second binary value with each of said output digital values which is on the other side of said first predetermined threshold value;

using said computer processor means to associate a discriminant value with each of said pixels, each discriminant value being chosen so that, for each training object, the dot product of the discimrinant values and the binary values is approximately a preetermined nonzero constant value;

repeating steps (a)–(d) for said object; and using said computer processor means to compare the dot product of said discriminant values and the binary values for said object to said predetermined nonzero constant value;

wherein said image of said object may be shifted in at least one direction from a reference position, and wherein said method further comprises the steps of:

using said computer processor means to associate a filter value with at least some of said pixels, each filter value being chosen so that the dot product of the filter values and the binary values for said object is proportional to the amount by which said object is shifted from said reference position.

10. The method defined in claim 9 further comprising the step of:

using said computer processor means to utilize the dot product of the filter values and the binary values for said object to register the binary values for said product within said reference position.

11. The method defined in claim 9 wherein said filter values collectively comprise a filter iamge F, and wherein said method further comprises the steps of:

using said computer processor means to select a training object which is in registration with said reference position;

using said computer processor means to select at least a portion of the binary values associated with said selected training object to produce a plurality of data sets in each of which said selected binary values are shifted by a respective one of a plurality of predetermined amounts parallel to said direction;

using said computer processor means to convert each of said data sets to a respective one of a plurality of eigenimages $\Phi^{(j)}$, all of said eigenimages being orthogonal to one another; and using said computer processor means to form said filter image from a truncated linear combination of said eigenimages.

12. The method defined in claim 11 wherein the ith data set is given by $\underline{J}^{(i)}$, and wherein said method further comprises the step of:

using said computer processor means to compute each of said eigenimages as in the equation:

$$\Phi^{(j)} = \sum_{i=1}^{m} \underline{J}^{(i)} B_{ij}$$

where m is the total number of data sets and the transformation matrix $\underline{B}$ is orthogonal.

13. The method defined in claim 12 wherein said step of forming said filter image from a truncated linear combination of said eigenimages comprises the step of:

using said computer processor means to compute said filter image as in the equation:

$$\underline{F} = \sum_{j=1}^{s} C_j \underline{\Phi}^{(j)}$$

where s is an integer less than or equal to m.

14. The method defined in claim 13 further comprising the step of:

using said computer processor means to select the value of s for the equation in claim 13 which gives the minimum value for V(s) in the equation:

$$V(s) = \frac{1}{(m-s)^2} \left\{ \sum_{i=1}^{m} \delta_i^2 - \sum_{j=1}^{s} \left[ \sum_{i=1}^{m} \delta_i B_{ij} \right]^2 \right\}$$

where $\delta_i$ is the amount by which the ith data set is shifted from said reference position.

15. The method defined in claim 14 further comprising the step of:

using said computer processor means to compute the value $C_j$ for the equation of claim 13 as in the equation:

$$C_j = \frac{1}{\gamma_j} \sum_{i=1}^{m} \delta_i B_{ij}$$

where the eigenvalues $\gamma_j$ are the diagonal elements of a matrix $\underline{\underline{G}}$ given by the equation $\underline{\underline{A}} \cdot \underline{\underline{B}} = \underline{\underline{B}} \cdot \underline{\underline{G}}$, where $\underline{\underline{A}}$ is the real, symmetric matrix given by the dot product of every possible data set pair, and the transformation matrix $\underline{\underline{B}}$ is such that $\underline{\underline{B}} \cdot \underline{\underline{B}}^+ = \underline{\underline{B}}^+ \cdot \underline{\underline{B}} = \underline{\underline{1}}$.

16. The method defined in claim 15 wherein said eigenimages are ordered such that $\gamma_1 > \gamma_2 > \gamma_3 > \ldots \geq \gamma_n$.

17. The method defined in claim 9 wherein said filter values are additionally chosen so that the sum of the squares of the filter values is approximately minimized.

18. Apparatus for determining whether or not a surface of an object has substantially the same appearance as the corresponding surface of a plurality of training objects comprising:
  means for, for each training object, (a) forming a two-dimensional image of said surface, (b) subdividing said two-dimensional image into a plurality of pixels, (c) digitizing each of said pixels by associating with each pixel an output digital value proportional to an optical characteristic of the associated pixel, and (d) binarizing each of said output digital values by associating a first binary value with each of said output digital values which is on one side of a first predetermined threshold value and by associating a second binary value with each of said output digital values which is on the other side of said first predetermined threshold value;
  means for associating a discriminant value with each of said pixels, each discriminant value being chosen so that, for each training object, the dot product of the discriminant values and the binary values is approximately a predetermined nonzero constant value;
  means for repeating functions (a)–(d) with respect to said object; and
  means for comparing the dot product of said discriminant values and the binary values for said object to said predetermined nonzero constant value;
  wherein said image of said object may be shifted in at least one direction from a reference position, and wherein said apparatus further comprises:
  means for associating a filter value with at least some of said pixels, each filter value being chosen so that the dot product of the filter values and the binary values for said object is proportional to the amount by which said object is shifted from said reference position.

19. The apparatus defined in claim 18 further comprising:
  means for using the dot product of the filter values and the binary values for said object to register the binary values for said product with said reference position.

20. The apparatus defined in claim 18 wherein said filter values collectively comprise a filter image $\underline{F}$, and wherein said apparatus further comprises:
  means for selecting a training object which is in registration with said reference position;
  means for selecting at least a portion of the binary values associated with said selected training object to produce a plurality of data sets in each of which said selected binary values are shifted by a respective one of a plurality of predetermined amounts parallel to said direction;
  means for converting each of said data sets to a respective one of a plurality of eigenimages $\Phi^{(j)}$, all of said eigenimages being orthogonal to one another; and
  means for forming said filter image from a truncated linear combination of said eigenimages.

21. The apparatus defined in claim 20 wherein the ith data set is given by $\underline{J}^{(i)}$, and wherein said apparatus further comprises:
  means for computing each of said eigenimages as in the equation:

$$\Phi^{(j)} = \sum_{i=1}^{m} \underline{J}^{(i)} B_{ij}$$

where m is the total number of data sets and the transformation matrix B is orthogonal.

22. The apparatus defined in claim 21 wherein said means for forming said filter image from a truncated linear combination of said eigenimages comprises:
  means for computing said filter image as in the equation:

$$\underline{F} = \sum_{j=1}^{s} C_j \underline{\Phi}^{(j)}$$

where s is an integer less than or equal to m.

23. The apparatus defined in claim 22 further comprising:
  means for selecting the value of s for the equation in claim 22 which gives the minimum value for V(s) in the equation:

$$V(s) = \frac{1}{(m-s)^2} \left\{ \sum_{i=1}^{m} \delta_i^2 - \sum_{j=1}^{s} \left[ \sum_{i=1}^{m} \delta_i B_{ij} \right]^2 \right\}$$

where $\delta_i$ is the amount by which the ith data set is shifted from said reference position.

24. The apparatus defined in claim 23 further comprising:
  means for computing the value $C_j$ for the equation of claim 22 as in the equation:

$$C_j = \frac{1}{\gamma_j} \sum_{i=1}^{m} \delta_i B_{ij}$$

where the eigenvalues $\gamma_j$ are the diagonal elements of a matrix $\underline{\underline{G}}$ given by the equation $\underline{\underline{A}} \cdot \underline{\underline{B}} = \underline{\underline{B}} \cdot \underline{\underline{G}}$, where A is the real, symmetric matrix given by the dot product of every possible data set pair, and the transformation matrix B is such that $\underline{\underline{B}} \cdot \underline{\underline{B}}^+ = \underline{\underline{B}}^+ \cdot \underline{\underline{B}} = \underline{\underline{1}}$.

25. The apparatus defined in claim 24 wherein said eigenimages are ordered such that $\gamma_1 > \gamma_2 > \gamma_3 > \ldots \geq \gamma_n$.

26. The apparatus defined in claim 18 wherein said filter values are additionally chosen so that the sum of the squares of the filter values is approximately minimized.

27. The method of determining whether or not a surface of an object has substantially the same appearance as the corresponding surface of a plurality of training objects, said method comprising the steps of:

for each training object, (a) forming a two-dimensional image of said surface, (b) using computer procsesor means to subdivide said two-dimensional image into a plurality of pixels, (c) using said computer processor means to digitize each of said pixels by associating with each pixel an output digital value proportional to an optical characteristic of the associated pixle, and (d) using said computer processor means to binarize each of said output digital values by associating a first binary value with each of said output digital values which is on one side of a first predetermined threshold value and by associating a second binary value with each of said output digital values which is on the other side of said first predetermined threshold value;

using said computer processor means to associate a discriminant value with each of said pixels, each dicriminant value being chosen so that, for each training object, the dot product of the disciminant values and the binary values is approximately a predetermined nonzero constant value;

repeating steps (a)-(d) for said object; and using said computer processor means to compare the dot product of said discriminant values and the binary values for said object to said predetermined nonzero constant value;

wherein all of the foregoing steps are performed separately for each of a plurality of different segments of the surface of said training objects and said object.

28. The method of determining whether or not a surface of each of a plurality of successive objects has substantially the same appearance as the corresponding surface of at least some of the preceding objects in the succession, said method comprising the steps of:

forming a two-dimensional image of said surface of each object in said succession;

using computer processor means to digitize each of said two-dimensional images;

using said computer processor means to utilize the digitized image of the surface of said first object in said succession to form a digitized discriminant image in which the digital values are related to the digital values in the digitized image of the surface of said first object by a predetermined proportionality value;

for at least some of said objects after said first object in said succession, using said computer processor means to replace the digital values in said digitized discriminant image with updated digital values respectively equal to the discriminant image digital values prior to replacement plus an amount proportional to a function of the dot product of the digitized discirminant image prior to replacement and the digitized image of the surface of said object on which said replacement is being based; and for at least some of said objects after said first object in said succession, using said computer processor means to compare the dot product of said digitized disciminant image and said digitized image of the surface of said object to a predetermined constant value.

29. The method defined in claim 28 wherein said proportionality value is approximately equal to the reciprocal of the square root of the sum of the squares of the digital values in the digitized image of the surface of said first object.

30. The method defined in claim 29 wherein said amount proportional to a function of teh dot product of the digitized discriminant image prior to replacement and the digitized image of the surface of said object on which said replacement is being based is given by the expression:

$$\delta e_i \frac{\underline{I}^{(i)}}{|\underline{I}^{(i)}|}$$

where $\underline{I}^{(i)}$ is the diqitized image on which said replacement is being based, where $|\underline{I}^{(i)}|$, is equal to the square root of the sum of the squares of the digitized values in the digitized image of the surface of said first object, where $$e_i = 1 - \underline{F}^{(i-1)} \cdot \frac{\underline{I}^{(i)}}{|\underline{I}^{(i)}|}$$

where $\underline{F}^{(i-1)}$ is the digitized discriminant image prior to replacement, and where $\delta$ is a predetermined learning parameter.

31. The method defined in claim 30 wherein $\delta$ has a value in the range from about 0 to about 2.

32. The method defined in claim 31 wherein $\delta$ is approximately 1.

33. The method defined in claim 28 wherein, for any object after said first object for which both said using said computer processor means to replace and using said computer processor means to comapre steps may be performed, said using said computer processor means to replace step is performed only if the results of said using said computer processor means to comapre step indicate that said dot product is within a predetermined range of said predetermined constant value.

34. The method defined in claim 28 wherein said using said computer processor means to compare step is performed only on objects following an initial subplurality of said objects.

35. The method defined in claim 28 wherein said using said computer processor means to replace step is performed only with respect to objects in an initial subplurality of said objects.

36. The method defined in claim 28 wherein said step of using said computer processor means to digitize each of said two-dimensional images comprises the steps of:

using said computer processor means to subdivide said image into a plurality of pixels;

using said computer processor means to digitize each of said pixels by associating with each pixel an output digital value proportional to an optical characteristic of the associated pixel; and using said computer processor means to binarize each of said output digital values by associating a first binary value with each of said output digital values which is on a first side of a first predetermined threshold value and by associating a second binary value with each of said output digital values which is on the other side of said first predetermined threshold value.

37. The method defined in claim 28 further comprising the step of:

using said computer processor means to subdivide each of said two-dimensional images into a plurality of segments and using said computer processor means to perform said steps of using said computer processor means to utilize, using said computer processor means to replace, and usign said computer processor means to compare separately with respect to each of said segments.

38. Apparatus for determining whether or not a surface of each of a plurality of successive objects has substantially the same appearance as the corresponding surface of at least some of the preceding objects in the succession, said apparatus comprising:
  means for forming a two-dimensional image of said surface of each object in said succession;
  means for digitizing each of said twodimensional images;
  means for using the digitized image of the surface of said first object in said succession to form a digitized discriminant image in which the digital values are related to the digital values in the digitized image of the surface of said first object by a predetermined proportionality value;
  means for, for at least some of said objects after said first object in said succession, replacing the digital values in said digitized discriminant image with updated digital values respectively equal to the discriminant image digital values prior to replacement plus an amount proportional to a function of the dot product of the digitized discriminant image prior to replacement and the digitized image of the surface of said object on which said replacement is being based; and
  means for, for at least some of said objects after said first object in said succession, comparing the dot product of said digitized discriminant image and said digitized image of the surface of said object to a predetermined constant value.

39. The apparatus defined in claim 38 wherein said proportionality value is approximately equal to the reciprocal of the square root of the sum of the squares of the digital values in the digitized image of the surface of said first object.

40. The apparatus defined in claim 39 wherein said amount proportional to a function of the dot product of the digitized discriminant image prior to replacement and the digitized image of the surface of said object on which said replacement is being based is given by the expression:

$$\delta e_i \frac{\underline{I}^{(i)}}{|I^{(i)}|}$$

where $I^{(i)}$ is the digitized image on which said replacement is being based, where $|I^{(i)}|$, is equal to the square root of the sum of the squares of the digitized values in the digitized image of the surface of said first object, where $$e_i = 1 - \underline{F}^{(i-1)} \cdot \frac{\underline{I}^{(i)}}{|I^{(i)}|}$$

where $\underline{F}^{(i-1)}$ is the digitized discriminant image prior to replacement, and where $\delta$ is a predetermined learning parameter.

41. The apparatus defined in claim 40 wherein $\delta$ has a value in the range from about 0 to about 2.

42. The apparatus defined in claim 41 wherein $\delta$ is approximately 1.

43. The apparatus defined in claim 38 wherein, for any object after said first object for which both said replacing and comparing functions may be performed, said replacing function is performed only if the results of said comparing function indicate that said dot product is within a predetermined range of said predetermined constant value.

44. The apparatus defined in claim 38 wherein said comparing function is performed only on objects following an initial subplurality of said objects.

45. The apparatus defined in claim 38 wherein said replacing function is performed only with respect to objects in an initial subplurality of said objects.

46. The apparatus defined in claim 38 wherein said means for digitizing each of said two-dimensional images comprises:
  means for subdividing said image into a plurality of pixels;
  means for digitizing each of said pixels by associating with each pixel an output digital value proportional to an optical characteristic of the associated pixel; and
  means for binarizing each of said output digital values by associating a first binary value with each of said output digital values which is on a first side of a first predetermined threshold value and by associating a second binary value with each of said output digital values which is on the other side of said first predetermined threshold value.

47. The apparatus defined in claim 38 further comprising:
  means for subdividing each of said twodimensional images into a plurality of segments and performing said functions of using, replacing, and comparing separately with respect to each of said segments.

* * * * *